(12) United States Patent
Neto

(10) Patent No.: US 9,907,745 B2
(45) Date of Patent: Mar. 6, 2018

(54) COSMETIC COMPOSITIONS AND METHOD OF MAKING THE SAME

(71) Applicant: KFS SKINCARE, INC., Huntington, WV (US)

(72) Inventor: Walter De Paula Neto, Lavalette, WV (US)

(73) Assignee: SERUCELL CORPORATION, Palo Alto, CA (US)

( * ) Notice: Subject to any disclaimer, the term of this patent is extended or adjusted under 35 U.S.C. 154(b) by 186 days.

(21) Appl. No.: 14/597,796

(22) Filed: Jan. 15, 2015

(65) Prior Publication Data

US 2015/0196484 A1    Jul. 16, 2015

Related U.S. Application Data

(60) Provisional application No. 61/927,674, filed on Jan. 15, 2014.

(51) Int. Cl.
| | |
|---|---|
| A61K 35/32 | (2015.01) |
| A61K 35/36 | (2015.01) |
| A61K 8/98 | (2006.01) |
| A61Q 19/08 | (2006.01) |
| A61K 8/67 | (2006.01) |
| A61Q 19/00 | (2006.01) |
| A61Q 17/04 | (2006.01) |

(52) U.S. Cl.
CPC ............. *A61K 8/981* (2013.01); *A61K 8/671* (2013.01); *A61K 8/676* (2013.01); *A61K 8/985* (2013.01); *A61Q 17/04* (2013.01); *A61Q 19/00* (2013.01); *A61Q 19/007* (2013.01); *A61Q 19/08* (2013.01); *A61K 2800/70* (2013.01)

(58) Field of Classification Search
None
See application file for complete search history.

(56) References Cited

U.S. PATENT DOCUMENTS

| | | | |
|---|---|---|---|
| 4,016,036 A | 4/1977 | Green et al. | |
| 5,561,107 A | 10/1996 | Jaynes et al. | |
| 6,191,110 B1 | 2/2001 | Jaynes et al. | |
| 7,118,746 B1 | 10/2006 | Naughton et al. | |
| 8,138,147 B2 | 3/2012 | Naughton et al. | |
| 8,246,969 B2 | 8/2012 | Engles et al. | |
| 8,246,971 B2 | 8/2012 | Engles et al. | |
| 8,268,336 B2 | 9/2012 | Engles et al. | |
| 8,361,485 B2 | 1/2013 | Naughton et al. | |
| 8,476,231 B2 | 7/2013 | Naughton et al. | |
| 8,518,422 B2 | 8/2013 | Monks et al. | |
| 2001/0048917 A1 | 12/2001 | Hoeffler et al. | |
| 2004/0116356 A1 | 6/2004 | Malik | |
| 2009/0202654 A1* | 8/2009 | Nixon | A61K 8/985 424/574 |
| 2011/0177015 A1* | 7/2011 | Friedlander | A61K 8/983 424/70.1 |

FOREIGN PATENT DOCUMENTS

| | | |
|---|---|---|
| CA | 2367281 A1 | 9/1999 |
| EP | 1375646 A1 | 2/2004 |
| WO | WO 2006014089 A1 | 2/2006 |
| WO | WO 2007005659 A2 | 1/2007 |
| WO | WO 2010086754 A2 | 8/2010 |
| WO | WO 2011138687 A2 | 11/2011 |

OTHER PUBLICATIONS

Berse et al. (1999) Clin. Exp. Immunol. 115: 176-182.*
Garner(1998) Plastic and Reconstructive Surgery, vol. 102, No. 1, 135-139.*
Ghaffari et al. (2009) J. Invest. Dermatol. vol. 129, 340-347.*
Hawley-Nelson (1980) J. Invest. Dermatol. 75: 176-182.*
Kubo et al. (1984) J. Invest. Dermatol. 82: 580-586.*
Li et al. (1010) FEBS J. 277: 3688-3698.*
Lim et al. (2002) Am. J. Physiol. Cell Physiol. 283: C212-C222.*
Wong et al. (2007) British Journal of Dermatology 156: 1149-1155.*

* cited by examiner

*Primary Examiner* — Christopher R Tate
*Assistant Examiner* — Russell G Fiebig
(74) *Attorney, Agent, or Firm* — Andrew D. Wright; Roberts Mlotkowski Safran Cole & Calderon, P.C.

(57) ABSTRACT

The present invention generally relates to cosmetic compositions comprising serum derived from cultured keratinocyte and fibroblast cells. The invention also relates to methods of producing serum for use in the cosmetic compositions through novel cell culture techniques.

5 Claims, 19 Drawing Sheets

| # | SAMPLE ID | USER NAME | DATE AND TIME | PROTEIN CONC. | UNIT | A280 | 260/280 | SAMPLE TYPE |
|---|---|---|---|---|---|---|---|---|
| 1 | RPMI 1 | ANALYTICAL LAB | 10/8/2013 12:09:25 PM | 0.442 | mg/ml | 0.442 | 1.00 | 1 Abs = 1 mg / mL |
| 2 | RPMI 2 | ANALYTICAL LAB | 10/8/2013 12:10:39 PM | 0.445 | mg/ml | 0.445 | 1.00 | 1 Abs = 1 mg / mL |
| 3 | RPMI 3 | ANALYTICAL LAB | 10/8/2013 12:11:22 PM | 0.448 | mg/ml | 0.448 | 1.00 | 1 Abs = 1 mg / mL |
| 4 | CM1-045 1 | ANALYTICAL LAB | 10/8/2013 12:17:05 PM | 0.515 | mg/ml | 0.515 | 0.82 | 1 Abs = 1 mg / mL |
| 5 | CM1-045 2 | ANALYTICAL LAB | 10/8/2013 12:17:50 PM | 6.842 | mg/ml | 6.842 | 1.19 | 1 Abs = 1 mg / mL |
| 6 | CM1-045 2 | ANALYTICAL LAB | 10/8/2013 12:19:41 PM | 0.505 | mg/ml | 0.505 | 0.81 | 1 Abs = 1 mg / mL |
| 7 | CM1-045 3 | ANALYTICAL LAB | 10/8/2013 12:20:50 PM | 0.514 | mg/ml | 0.514 | 0.81 | 1 Abs = 1 mg / mL |
| 8 | CM1-045 4 | ANALYTICAL LAB | 10/8/2013 12:21:49 PM | 0.526 | mg/ml | 0.526 | 0.81 | 1 Abs = 1 mg / mL |
| 9 | CM1-045 5 | ANALYTICAL LAB | 10/8/2013 12:22:36 PM | 0.531 | mg/ml | 0.531 | 0.80 | 1 Abs = 1 mg / mL |
| 10 | CM1-045 6 | ANALYTICAL LAB | 10/8/2013 12:23:20 PM | 0.517 | mg/ml | 0.517 | 0.81 | 1 Abs = 1 mg / mL |
| 11 | CM1-022 1 | ANALYTICAL LAB | 10/8/2013 12:39:24 PM | 0.481 | mg/ml | 0.481 | 0.80 | 1 Abs = 1 mg / mL |
| 12 | CM1-022 2 | ANALYTICAL LAB | 10/8/2013 12:40:02 PM | 0.500 | mg/ml | 0.500 | 0.78 | 1 Abs = 1 mg / mL |
| 13 | CM1-022 3 | ANALYTICAL LAB | 10/8/2013 12:40:39 PM | 0.502 | mg/ml | 0.502 | 0.80 | 1 Abs = 1 mg / mL |
| 14 | CM1-022 4 | ANALYTICAL LAB | 10/8/2013 12:41:11 PM | 0.506 | mg/ml | 0.506 | 0.79 | 1 Abs = 1 mg / mL |
| 15 | CM1-NAF 1 | ANALYTICAL LAB | 10/8/2013 12:42:25 PM | 0.542 | mg/ml | 0.542 | 0.81 | 1 Abs = 1 mg / mL |
| 16 | CM1-NAF 1 | ANALYTICAL LAB | 10/8/2013 12:42:49 PM | 0.549 | mg/ml | 0.549 | 0.78 | 1 Abs = 1 mg / mL |
| 17 | CM1-NAF 3 | ANALYTICAL LAB | 10/8/2013 12:43:38 PM | 0.528 | mg/ml | 0.528 | 0.77 | 1 Abs = 1 mg / mL |
| 18 | CM1-NAF 4 | ANALYTICAL LAB | 10/8/2013 12:44:17 PM | 0.537 | mg/ml | 0.537 | 0.78 | 1 Abs = 1 mg / mL |
| 19 | CM1-NAF 5 | ANALYTICAL LAB | 10/8/2013 12:45:06 PM | 0.527 | mg/ml | 0.527 | 0.79 | 1 Abs = 1 mg / mL |
| 20 | CM1-NAF 6 | ANALYTICAL LAB | 10/8/2013 12:45:40 PM | 0.534 | mg/ml | 0.534 | 0.78 | 1 Abs = 1 mg / mL |
| 21 | CM1-NAF 6 | ANALYTICAL LAB | 10/8/2013 12:46:20 PM | 0.551 | mg/ml | 0.551 | 0.78 | 1 Abs = 1 mg / mL |
| 22 | CM1-NAF 7 | ANALYTICAL LAB | 10/8/2013 12:47:01 PM | 0.550 | mg/ml | 0.550 | 0.78 | 1 Abs = 1 mg / mL |
| 23 | CM1-NAF 7 | ANALYTICAL LAB | 10/8/2013 12:47:29 PM | 0.560 | mg/ml | 0.560 | 0.78 | 1 Abs = 1 mg / mL |
| 24 | CM1-NAF 7 | ANALYTICAL LAB | 10/8/2013 12:48:02 PM | 0.545 | mg/ml | 0.545 | 0.77 | 1 Abs = 1 mg / mL |
| 25 | CM1-NAF 7 | ANALYTICAL LAB | 10/8/2013 12:48:36 PM | 0.554 | mg/ml | 0.554 | 0.78 | 1 Abs = 1 mg / mL |
| 26 | CM2-0.45 1 | ANALYTICAL LAB | 10/8/2013 12:49:52 PM | 0.600 | mg/ml | 0.600 | 0.76 | 1 Abs = 1 mg / mL |
| 27 | CM2-0.45 1 | ANALYTICAL LAB | 10/8/2013 12:50:24 PM | 0.633 | mg/ml | 0.633 | 0.80 | 1 Abs = 1 mg / mL |
| 28 | CM2-0.45 1 | ANALYTICAL LAB | 10/8/2013 12:50:53 PM | 0.625 | mg/ml | 0.625 | 0.80 | 1 Abs = 1 mg / mL |
| 29 | CM2-0.45 1 | ANALYTICAL LAB | 10/8/2013 12:51:16 PM | 0.632 | mg/ml | 0.632 | 0.81 | 1 Abs = 1 mg / mL |
| 30 | CM2-0.45 1 | ANALYTICAL LAB | 10/8/2013 12:51:54 PM | 0.649 | mg/ml | 0.649 | 0.82 | 1 Abs = 1 mg / mL |
| 31 | CM2-0.45 1 | ANALYTICAL LAB | 10/8/2013 12:52:22 PM | 0.625 | mg/ml | 0.625 | 0.81 | 1 Abs = 1 mg / mL |
| 32 | CM2-0.45 1 | ANALYTICAL LAB | 10/8/2013 12:53:00 PM | 0.639 | mg/ml | 0.639 | 0.81 | 1 Abs = 1 mg / mL |
| 33 | CM2-0.45 1 | ANALYTICAL LAB | 10/8/2013 12:53:25 PM | 0.625 | mg/ml | 0.625 | 0.81 | 1 Abs = 1 mg / mL |
| 34 | CM2-0.22 | ANALYTICAL LAB | 10/8/2013 12:54:22 PM | 0.630 | mg/ml | 0.630 | 0.80 | 1 Abs = 1 mg / mL |
| 35 | CM2-0.22 | ANALYTICAL LAB | 10/8/2013 12:54:50 PM | 0.554 | mg/ml | 0.554 | 0.80 | 1 Abs = 1 mg / mL |

FROM FIG. 1A

| # | SAMPLE ID | USER NAME | DATE AND TIME | PROTEIN CONC. | UNIT | A280 | 260/280 | SAMPLE TYPE |
|---|---|---|---|---|---|---|---|---|
| 36 | CM2-0.22 | ANALYTICAL LAB | 10/8/2013 12:55:18 PM | 0.570 | mg/ml | 0.570 | 0.81 | 1 Abs = 1 mg/mL |
| 37 | CM2-0.22 | ANALYTICAL LAB | 10/8/2013 12:55:46 PM | 0.599 | mg/ml | 0.599 | 0.81 | 1 Abs = 1 mg/mL |
| 38 | CM2-0.22 | ANALYTICAL LAB | 10/8/2013 12:56:27 PM | 0.604 | mg/ml | 0.604 | 0.79 | 1 Abs = 1 mg/mL |
| 39 | CM2-0.22 | ANALYTICAL LAB | 10/8/2013 12:56:53 PM | 0.592 | mg/ml | 0.592 | 0.81 | 1 Abs = 1 mg/mL |
| 40 | CM2-0.22 | ANALYTICAL LAB | 10/8/2013 12:57:17 PM | 0.586 | mg/ml | 0.586 | 0.80 | 1 Abs = 1 mg/mL |
| 41 | CM2-0.22 | ANALYTICAL LAB | 10/8/2013 12:58:11 PM | 0.606 | mg/ml | 0.606 | 0.80 | 1 Abs = 1 mg/mL |
| 42 | CM2-0.22 | ANALYTICAL LAB | 10/8/2013 12:59:00 PM | 0.621 | mg/ml | 0.621 | 0.81 | 1 Abs = 1 mg/mL |
| 43 | CM2-0.22 | ANALYTICAL LAB | 10/8/2013 12:59:33 PM | 0.613 | mg/ml | 0.613 | 0.79 | 1 Abs = 1 mg/mL |
| 44 | CM2-0.22 | ANALYTICAL LAB | 10/8/2013 1:00:03 PM | 0.601 | mg/ml | 0.601 | 0.81 | 1 Abs = 1 mg/mL |
| 45 | CM2-0.22 | ANALYTICAL LAB | 10/8/2013 1:00:37 PM | 0.612 | mg/ml | 0.612 | 0.80 | 1 Abs = 1 mg/mL |
| 46 | CM2-0.22 | ANALYTICAL LAB | 10/8/2013 1:01:22 PM | 0.615 | mg/ml | 0.615 | 0.81 | 1 Abs = 1 mg/mL |
| 47 | CM2-NAF | ANALYTICAL LAB | 10/8/2013 1:02:22 PM | 0.696 | mg/ml | 0.696 | 0.82 | 1 Abs = 1 mg/mL |
| 48 | CM2-NAF | ANALYTICAL LAB | 10/8/2013 1:03:04 PM | 0.746 | mg/ml | 0.746 | 0.80 | 1 Abs = 1 mg/mL |
| 49 | CM2-NAF | ANALYTICAL LAB | 10/8/2013 1:03:37 PM | 0.658 | mg/ml | 0.658 | 0.78 | 1 Abs = 1 mg/mL |
| 50 | CM2-NAF | ANALYTICAL LAB | 10/8/2013 1:04:21 PM | 0.675 | mg/ml | 0.675 | 0.78 | 1 Abs = 1 mg/mL |
| 51 | CM2-NAF | ANALYTICAL LAB | 10/8/2013 1:04:50 PM | 0.676 | mg/ml | 0.676 | 0.80 | 1 Abs = 1 mg/mL |
| 52 | CM2-NAF | ANALYTICAL LAB | 10/8/2013 1:05:24 PM | 0.660 | mg/ml | 0.660 | 0.80 | 1 Abs = 1 mg/mL |
| 53 | CM2-NAF | ANALYTICAL LAB | 10/8/2013 1:05:49 PM | 0.653 | mg/ml | 0.653 | 0.77 | 1 Abs = 1 mg/mL |
| 54 | CM2-NAF | ANALYTICAL LAB | 10/8/2013 1:06:23 PM | 0.633 | mg/ml | 0.633 | 0.75 | 1 Abs = 1 mg/mL |
| 55 | CM2-NAF | ANALYTICAL LAB | 10/8/2013 1:06:47 PM | 0.656 | mg/ml | 0.656 | 0.76 | 1 Abs = 1 mg/mL |
| 56 | CM2-NAF | ANALYTICAL LAB | 10/8/2013 1:07:17 PM | 0.629 | mg/ml | 0.629 | 0.77 | 1 Abs = 1 mg/mL |
| 57 | CM2-NAF | ANALYTICAL LAB | 10/8/2013 1:07:45 PM | 0.656 | mg/ml | 0.656 | 0.79 | 1 Abs = 1 mg/mL |
| 58 | CM3-0.45 | ANALYTICAL LAB | 10/8/2013 1:08:49 PM | 0.671 | mg/ml | 0.671 | 0.79 | 1 Abs = 1 mg/mL |
| 59 | CM3-0.45 | ANALYTICAL LAB | 10/8/2013 1:09:20 PM | 0.638 | mg/ml | 0.638 | 0.79 | 1 Abs = 1 mg/mL |
| 60 | CM3-0.45 | ANALYTICAL LAB | 10/8/2013 1:09:45 PM | 0.658 | mg/ml | 0.658 | 0.79 | 1 Abs = 1 mg/mL |
| 61 | CM3-0.45 | ANALYTICAL LAB | 10/8/2013 1:10:13 PM | 0.657 | mg/ml | 0.657 | 0.80 | 1 Abs = 1 mg/mL |
| 62 | CM3-0.45 | ANALYTICAL LAB | 10/8/2013 1:10:37 PM | 0.655 | mg/ml | 0.655 | 0.80 | 1 Abs = 1 mg/mL |
| 63 | CM3-0.22 | ANALYTICAL LAB | 10/8/2013 1:11:35 PM | 0.641 | mg/ml | 0.641 | 0.79 | 1 Abs = 1 mg/mL |
| 64 | CM3-0.22 | ANALYTICAL LAB | 10/8/2013 1:11:54 PM | 0.595 | mg/ml | 0.595 | 0.79 | 1 Abs = 1 mg/mL |
| 65 | CM3-0.22 | ANALYTICAL LAB | 10/8/2013 1:12:21 PM | 0.613 | mg/ml | 0.613 | 0.79 | 1 Abs = 1 mg/mL |
| 66 | CM3-0.22 | ANALYTICAL LAB | 10/8/2013 1:12:54 PM | 0.624 | mg/ml | 0.624 | 0.79 | 1 Abs = 1 mg/mL |
| 67 | CM3-0.22 | ANALYTICAL LAB | 10/8/2013 1:13:26 PM | 0.618 | mg/ml | 0.618 | 0.78 | 1 Abs = 1 mg/mL |
| 68 | CM3-0.22 | ANALYTICAL LAB | 10/8/2013 1:13:49 PM | 0.617 | mg/ml | 0.617 | 0.78 | 1 Abs = 1 mg/mL |
| 69 | CM3-0.22 | ANALYTICAL LAB | 10/8/2013 1:14:17 PM | 0.622 | mg/ml | 0.622 | 0.78 | 1 Abs = 1 mg/mL |
| 70 | CM3-0.22 | ANALYTICAL LAB | 10/8/2013 1:14:46 PM | 0.616 | mg/ml | 0.616 | 0.78 | 1 Abs = 1 mg/mL |

FROM FIG. 1B

| # | SAMPLE ID | USER NAME | DATE AND TIME | PROTEIN CONC. | UNIT | A280 | 260/280 | SAMPLE TYPE |
|---|---|---|---|---|---|---|---|---|
| 71 | CM2-NAF | ANALYTICAL LAB | 10/8/2013 1:15:31 PM | 0.676 | mg/ml | 0.676 | 0.79 | 1 Abs = 1 mg / mL |
| 72 | CM2-NAF | ANALYTICAL LAB | 10/8/2013 1:15:55 PM | 0.686 | mg/ml | 0.686 | 0.80 | 1 Abs = 1 mg / mL |
| 73 | CM2-NAF | ANALYTICAL LAB | 10/8/2013 1:16:27 PM | 0.668 | mg/ml | 0.668 | 0.78 | 1 Abs = 1 mg / mL |
| 74 | CM2-NAF | ANALYTICAL LAB | 10/8/2013 1:17:01 PM | 0.688 | mg/ml | 0.688 | 0.78 | 1 Abs = 1 mg / mL |
| 75 | CM2-NAF | ANALYTICAL LAB | 10/8/2013 1:17:22 PM | 0.674 | mg/ml | 0.674 | 0.80 | 1 Abs = 1 mg / mL |
| 76 | CM2-NAF | ANALYTICAL LAB | 10/8/2013 1:17:46 PM | 0.672 | mg/ml | 0.672 | 0.78 | 1 Abs = 1 mg / mL |
| 77 | KREOTIN MEDIA | ANALYTICAL LAB | 10/8/2013 1:22:54 PM | 0.712 | mg/ml | 0.712 | 3.66 | 1 Abs = 1 mg / mL |
| 78 | KREOTIN MEDIA | ANALYTICAL LAB | 10/8/2013 1:23:23 PM | 0.797 | mg/ml | 0.797 | 3.38 | 1 Abs = 1 mg / mL |
| 79 | KREOTIN MEDIA | ANALYTICAL LAB | 10/8/2013 1:23:47 PM | 0.743 | mg/ml | 0.743 | 3.56 | 1 Abs = 1 mg / mL |
| 80 | KREOTIN MEDIA | ANALYTICAL LAB | 10/8/2013 1:24:09 PM | 0.727 | mg/ml | 0.727 | 3.62 | 1 Abs = 1 mg / mL |
| 81 | KREOTIN MEDIA | ANALYTICAL LAB | 10/8/2013 1:24:30 PM | 0.728 | mg/ml | 0.728 | 3.61 | 1 Abs = 1 mg / mL |
| 82 | KREOTIN MEDIA | ANALYTICAL LAB | 10/8/2013 1:24:56 PM | 0.734 | mg/ml | 0.734 | 3.62 | 1 Abs = 1 mg / mL |
| 83 | KREOTIN MEDIA | ANALYTICAL LAB | 10/8/2013 1:25:22 PM | 0.742 | mg/ml | 0.742 | 3.57 | 1 Abs = 1 mg / mL |
| 84 | KREOTIN MEDIA | ANALYTICAL LAB | 10/8/2013 1:25:34 PM | 0.745 | mg/ml | 0.745 | 3.57 | 1 Abs = 1 mg / mL |
| 85 | KCM-0.45 | ANALYTICAL LAB | 10/8/2013 1:26:41 PM | 0.479 | mg/ml | 0.479 | 3.68 | 1 Abs = 1 mg / mL |
| 86 | KCM-0.45 | ANALYTICAL LAB | 10/8/2013 1:27:15 PM | 0.477 | mg/ml | 0.477 | 3.71 | 1 Abs = 1 mg / mL |
| 87 | KCM-0.45 | ANALYTICAL LAB | 10/8/2013 1:27:52 PM | 0.470 | mg/ml | 0.470 | 3.74 | 1 Abs = 1 mg / mL |
| 88 | KCM-0.22 | ANALYTICAL LAB | 10/8/2013 1:28:28 PM | 0.715 | mg/ml | 0.715 | 3.71 | 1 Abs = 1 mg / mL |
| 89 | KCM-0.22 | ANALYTICAL LAB | 10/8/2013 1:28:53 PM | 0.715 | mg/ml | 0.715 | 3.73 | 1 Abs = 1 mg / mL |
| 90 | KCM-0.22 | ANALYTICAL LAB | 10/8/2013 1:29:16 PM | 0.721 | mg/ml | 0.721 | 3.70 | 1 Abs = 1 mg / mL |
| 91 | KCM-NAF | ANALYTICAL LAB | 10/8/2013 1:29:57 PM | 0.735 | mg/ml | 0.735 | 3.62 | 1 Abs = 1 mg / mL |
| 92 | KCM-NAF | ANALYTICAL LAB | 10/8/2013 1:30:20 PM | 0.790 | mg/ml | 0.790 | 3.52 | 1 Abs = 1 mg / mL |
| 93 | KCM-NAF | ANALYTICAL LAB | 10/8/2013 1:30:43 PM | 0.765 | mg/ml | 0.765 | 3.64 | 1 Abs = 1 mg / mL |
| 94 | KCM-NAF | ANALYTICAL LAB | 10/8/2013 1:31:06 PM | 0.791 | mg/ml | 0.791 | 3.55 | 1 Abs = 1 mg / mL |
| 95 | KCM-NAF | ANALYTICAL LAB | 10/8/2013 1:31:24 PM | 0.794 | mg/ml | 0.794 | 3.53 | 1 Abs = 1 mg / mL |

FIG. 1C

| # | SAMPLE ID | USER NAME | DATE AND TIME | PROTEIN CONC. | UNIT | A280 | 260/280 | SAMPLE TYPE |
|---|---|---|---|---|---|---|---|---|
| 1 | mem | ANALYTICAL LAB | 10/15/2013 1:34:27 PM | 0.627 | mg/ml | 0.627 | 0.74 | 1 Abs = 1 mg / mL |
| 2 | mem | ANALYTICAL LAB | 10/15/2013 1:34:58 PM | 0.643 | mg/ml | 0.643 | 0.72 | 1 Abs = 1 mg / mL |
| 3 | mem | ANALYTICAL LAB | 10/15/2013 1:35:22 PM | 0.643 | mg/ml | 0.643 | 0.73 | 1 Abs = 1 mg / mL |
| 4 | mem | ANALYTICAL LAB | 10/15/2013 1:35:46 PM | 0.633 | mg/ml | 0.633 | 0.74 | 1 Abs = 1 mg / mL |
| 5 | CM1.45 | ANALYTICAL LAB | 10/15/2013 1:36:32 PM | 0.983 | mg/ml | 0.983 | 0.76 | 1 Abs = 1 mg / mL |
| 6 | CM1.45 | ANALYTICAL LAB | 10/15/2013 1:36:55 PM | 0.974 | mg/ml | 0.974 | 0.75 | 1 Abs = 1 mg / mL |
| 7 | CM1.45 | ANALYTICAL LAB | 10/15/2013 1:37:17 PM | 0.984 | mg/ml | 0.984 | 0.76 | 1 Abs = 1 mg / mL |
| 8 | CM2.45 | ANALYTICAL LAB | 10/15/2013 1:38:17 PM | 0.665 | mg/ml | 0.665 | 0.79 | 1 Abs = 1 mg / mL |
| 9 | CM2.45 | ANALYTICAL LAB | 10/15/2013 1:38:41 PM | 0.664 | mg/ml | 0.664 | 0.78 | 1 Abs = 1 mg / mL |
| 10 | CM2.45 | ANALYTICAL LAB | 10/15/2013 1:39:01 PM | 0.651 | mg/ml | 0.651 | 0.79 | 1 Abs = 1 mg / mL |
| 11 | CM3.45 | ANALYTICAL LAB | 10/15/2013 1:39:34 PM | 0.753 | mg/ml | 0.753 | 0.76 | 1 Abs = 1 mg / mL |
| 12 | CM3.45 | ANALYTICAL LAB | 10/15/2013 1:39:58 PM | 0.804 | mg/ml | 0.804 | 0.75 | 1 Abs = 1 mg / mL |
| 13 | CM3.45 | ANALYTICAL LAB | 10/15/2013 1:40:23 PM | 0.746 | mg/ml | 0.746 | 0.77 | 1 Abs = 1 mg / mL |
| 14 | CM3.45 | ANALYTICAL LAB | 10/15/2013 1:40:43 PM | 0.747 | mg/ml | 0.747 | 0.78 | 1 Abs = 1 mg / mL |

FIG. 2

| # | SAMPLE ID | USER NAME | DATE AND TIME | PROTEIN CONC. | UNIT | A280 | 260/280 | SAMPLE TYPE |
|---|---|---|---|---|---|---|---|---|
| 1 | CONTROL MEDIA | ANALYTICAL LAB | 10/30/2013 10:14:59 AM | 0.505 | mg/ml | 0.505 | 0.88 | 1 Abs = 1 mg / mL |
| 2 | CONTROL MEDIA | ANALYTICAL LAB | 10/30/2013 10:15:53 AM | 0.514 | mg/ml | 0.514 | 0.90 | 1 Abs = 1 mg / mL |
| 3 | CONTROL MEDIA | ANALYTICAL LAB | 10/30/2013 10:16:28 AM | 0.516 | mg/ml | 0.516 | 0.89 | 1 Abs = 1 mg / mL |
| 4 | CM1 | ANALYTICAL LAB | 10/30/2013 10:17:45 AM | 0.648 | mg/ml | 0.648 | 1.08 | 1 Abs = 1 mg / mL |
| 5 | CM1 | ANALYTICAL LAB | 10/30/2013 10:18:15 AM | 0.662 | mg/ml | 0.662 | 1.07 | 1 Abs = 1 mg / mL |
| 6 | CM1 | ANALYTICAL LAB | 10/30/2013 10:18:38 AM | 0.657 | mg/ml | 0.657 | 1.07 | 1 Abs = 1 mg / mL |
| 7 | CM1 | ANALYTICAL LAB | 10/30/2013 10:19:07 AM | 0.655 | mg/ml | 0.655 | 1.07 | 1 Abs = 1 mg / mL |
| 8 | CM2 | ANALYTICAL LAB | 10/30/2013 10:20:13 AM | 0.737 | mg/ml | 0.737 | 1.03 | 1 Abs = 1 mg / mL |
| 9 | CM2 | ANALYTICAL LAB | 10/30/2013 10:20:44 AM | 0.736 | mg/ml | 0.736 | 1.03 | 1 Abs = 1 mg / mL |
| 10 | CM3 | ANALYTICAL LAB | 10/30/2013 10:21:47 AM | 0.871 | mg/ml | 0.871 | 0.94 | 1 Abs = 1 mg / mL |
| 11 | CM3 | ANALYTICAL LAB | 10/30/2013 10:22:12 AM | 0.870 | mg/ml | 0.870 | 0.94 | 1 Abs = 1 mg / mL |

FIG. 3

| # | SAMPLE ID | USER NAME | DATE AND TIME | PROTEIN CONC. | UNIT | A280 | 260/280 | SAMPLE TYPE |
|---|---|---|---|---|---|---|---|---|
| 1 | CM4 | ANALYTICAL LAB | 10/30/2013 11:08:29 AM | 0.639 | mg/ml | 0.639 | 0.97 | 1 Abs = 1 mg / mL |
| 2 | CM4 | ANALYTICAL LAB | 10/30/2013 11:09:07 AM | 0.647 | mg/ml | 0.647 | 0.97 | 1 Abs = 1 mg / mL |
| 3 | CM4 | ANALYTICAL LAB | 10/30/2013 11:10:20 AM | 0.649 | mg/ml | 0.649 | 0.98 | 1 Abs = 1 mg / mL |
| 4 | MIX4 | ANALYTICAL LAB | 10/30/2013 11:11:12 AM | 0.708 | mg/ml | 0.708 | 1.00 | 1 Abs = 1 mg / mL |
| 5 | MIX4 | ANALYTICAL LAB | 10/30/2013 11:11:49 AM | 0.703 | mg/ml | 0.703 | 1.00 | 1 Abs = 1 mg / mL |

FIG. 4

| # | SAMPLE ID | USER NAME | DATE AND TIME | PROTEIN CONC. | UNIT | A280 | 260/280 | SAMPLE TYPE |
|---|---|---|---|---|---|---|---|---|
| 1 | CONTROL | ANALYTICAL LAB | 10/31/2013 11:22:58 AM | 0.486 | mg/ml | 0.486 | 0.90 | 1 Abs = 1 mg / mL |
| 2 | CONTROL | ANALYTICAL LAB | 10/31/2013 11:23:33 AM | 0.525 | mg/ml | 0.525 | 0.89 | 1 Abs = 1 mg / mL |
| 3 | CONTROL | ANALYTICAL LAB | 10/31/2013 11:23:57 AM | 0.497 | mg/ml | 0.497 | 0.89 | 1 Abs = 1 mg / mL |
| 4 | CONTROL | ANALYTICAL LAB | 10/31/2013 11:24:22 AM | 0.495 | mg/ml | 0.495 | 0.89 | 1 Abs = 1 mg / mL |
| 5 | CM1 | ANALYTICAL LAB | 10/31/2013 11:25:15 AM | 0.657 | mg/ml | 0.657 | 1.07 | 1 Abs = 1 mg / mL |
| 6 | CM1 | ANALYTICAL LAB | 10/31/2013 11:25:39 AM | 0.635 | mg/ml | 0.635 | 1.08 | 1 Abs = 1 mg / mL |
| 7 | CM1 | ANALYTICAL LAB | 10/31/2013 11:26:09 AM | 0.639 | mg/ml | 0.639 | 1.08 | 1 Abs = 1 mg / mL |
| 8 | CM2 | ANALYTICAL LAB | 10/31/2013 11:26:57 AM | 0.732 | mg/ml | 0.732 | 1.02 | 1 Abs = 1 mg / mL |
| 9 | CM2 | ANALYTICAL LAB | 10/31/2013 11:27:17 AM | 0.722 | mg/ml | 0.722 | 1.02 | 1 Abs = 1 mg / mL |
| 10 | CM2 | ANALYTICAL LAB | 10/31/2013 11:27:43 AM | 0.718 | mg/ml | 0.718 | 1.02 | 1 Abs = 1 mg / mL |
| 11 | CM3 | ANALYTICAL LAB | 10/31/2013 11:28:31 AM | 0.864 | mg/ml | 0.864 | 0.93 | 1 Abs = 1 mg / mL |
| 12 | CM3 | ANALYTICAL LAB | 10/31/2013 11:28:59 AM | 0.859 | mg/ml | 0.859 | 0.93 | 1 Abs = 1 mg / mL |
| 13 | CM4 | ANALYTICAL LAB | 10/31/2013 11:30:00 AM | 0.666 | mg/ml | 0.666 | 0.96 | 1 Abs = 1 mg / mL |
| 14 | CM4 | ANALYTICAL LAB | 10/31/2013 11:30:24 AM | 0.645 | mg/ml | 0.645 | 0.98 | 1 Abs = 1 mg / mL |
| 15 | CM4 | ANALYTICAL LAB | 10/31/2013 11:30:51 AM | 0.644 | mg/ml | 0.644 | 0.98 | 1 Abs = 1 mg / mL |
| 16 | MIX ALL | ANALYTICAL LAB | 10/31/2013 11:31:35 AM | 0.722 | mg/ml | 0.722 | 1.00 | 1 Abs = 1 mg / mL |
| 17 | MIX ALL | ANALYTICAL LAB | 10/31/2013 11:31:59 AM | 0.716 | mg/ml | 0.716 | 1.00 | 1 Abs = 1 mg / mL |
| 18 | MIX ALL | ANALYTICAL LAB | 10/31/2013 11:32:34 AM | 0.711 | mg/ml | 0.711 | 1.00 | 1 Abs = 1 mg / mL |

FIG. 5

| # | SAMPLE ID | USER NAME | DATE AND TIME | PROTEIN CONC. | UNIT | A280 | 260/280 | SAMPLE TYPE |
|---|---|---|---|---|---|---|---|---|
| 1 | CONTROL | ANALYTICAL LAB | 10/31/2013 2:22:54 PM | 0.538 | mg/ml | 0.538 | 0.93 | 1 Abs = 1 mg / mL |
| 2 | CONTROL | ANALYTICAL LAB | 10/31/2013 2:23:31 PM | 0.537 | mg/ml | 0.537 | 0.94 | 1 Abs = 1 mg / mL |
| 3 | cm1 | ANALYTICAL LAB | 10/31/2013 2:24:03 PM | 0.955 | mg/ml | 0.955 | 1.03 | 1 Abs = 1 mg / mL |
| 4 | cm1 | ANALYTICAL LAB | 10/31/2013 2:24:29 PM | 0.919 | mg/ml | 0.919 | 1.02 | 1 Abs = 1 mg / mL |
| 5 | cm1 | ANALYTICAL LAB | 10/31/2013 2:24:49 PM | 0.911 | mg/ml | 0.911 | 1.03 | 1 Abs = 1 mg / mL |
| 6 | cm1 | ANALYTICAL LAB | 10/31/2013 2:25:18 PM | 0.918 | mg/ml | 0.918 | 1.02 | 1 Abs = 1 mg / mL |
| 7 | cm2 | ANALYTICAL LAB | 10/31/2013 2:26:01 PM | 0.980 | mg/ml | 0.980 | 0.98 | 1 Abs = 1 mg / mL |
| 8 | cm2 | ANALYTICAL LAB | 10/31/2013 2:26:37 PM | 0.980 | mg/ml | 0.980 | 0.97 | 1 Abs = 1 mg / mL |
| 9 | cm3 | ANALYTICAL LAB | 10/31/2013 2:27:25 PM | 1.143 | mg/ml | 1.143 | 0.94 | 1 Abs = 1 mg / mL |
| 10 | cm3 | ANALYTICAL LAB | 10/31/2013 2:28:10 PM | 1.054 | mg/ml | 1.054 | 0.93 | 1 Abs = 1 mg / mL |
| 11 | cm3 | ANALYTICAL LAB | 10/31/2013 2:28:32 PM | 1.040 | mg/ml | 1.040 | 0.92 | 1 Abs = 1 mg / mL |
| 12 | cm3 | ANALYTICAL LAB | 10/31/2013 2:28:52 PM | 1.037 | mg/ml | 1.037 | 0.92 | 1 Abs = 1 mg / mL |
| 13 | cm4 | ANALYTICAL LAB | 10/31/2013 2:29:32 PM | 0.846 | mg/ml | 0.846 | 0.97 | 1 Abs = 1 mg / mL |
| 14 | cm4 | ANALYTICAL LAB | 10/31/2013 2:29:53 PM | 0.840 | mg/ml | 0.840 | 0.98 | 1 Abs = 1 mg / mL |
| 15 | cm4 | ANALYTICAL LAB | 10/31/2013 2:30:12 PM | 0.848 | mg/ml | 0.848 | 0.98 | 1 Abs = 1 mg / mL |
| 16 | MIX | ANALYTICAL LAB | 10/31/2013 2:30:50 PM | 1.732 | mg/ml | 1.732 | 1.11 | 1 Abs = 1 mg / mL |
| 17 | MIX | ANALYTICAL LAB | 10/31/2013 2:31:11 PM | 0.917 | mg/ml | 0.917 | 0.99 | 1 Abs = 1 mg / mL |
| 18 | MIX | ANALYTICAL LAB | 10/31/2013 2:31:31 PM | 0.898 | mg/ml | 0.898 | 0.98 | 1 Abs = 1 mg / mL |
| 19 | MIX | ANALYTICAL LAB | 10/31/2013 2:31:51 PM | 0.910 | mg/ml | 0.910 | 1.00 | 1 Abs = 1 mg / mL |
| 20 | MIX | ANALYTICAL LAB | 10/31/2013 2:32:22 PM | 0.908 | mg/ml | 0.908 | 0.99 | 1 Abs = 1 mg / mL |

FIG. 6

| # | SAMPLE ID | USER NAME | DATE AND TIME | PROTEIN CONC. | UNIT | A280 | 260/280 | SAMPLE TYPE |
|---|---|---|---|---|---|---|---|---|
| 1 | CONTROL | ANALYTICAL LAB | 11/5/2013 10:15:41 AM | 0.489 | mg/ml | 0.489 | 0.89 | 1 Abs = 1 mg / mL |
| 2 | CONTROL | ANALYTICAL LAB | 11/5/2013 10:16:10 AM | 0.495 | mg/ml | 0.495 | 0.90 | 1 Abs = 1 mg / mL |
| 3 | CONTROL | ANALYTICAL LAB | 11/5/2013 10:16:35 AM | 0.495 | mg/ml | 0.495 | 0.90 | 1 Abs = 1 mg / mL |
| 4 | MIX 1 2 3 | ANALYTICAL LAB | 11/5/2013 10:17:36 AM | 0.746 | mg/ml | 0.746 | 1.00 | 1 Abs = 1 mg / mL |
| 5 | MIX 1 2 3 | ANALYTICAL LAB | 11/5/2013 10:17:59 AM | 0.740 | mg/ml | 0.740 | 1.00 | 1 Abs = 1 mg / mL |
| 6 | MIX 1 2 3 | ANALYTICAL LAB | 11/5/2013 10:18:21 AM | 0.736 | mg/ml | 0.736 | 1.00 | 1 Abs = 1 mg / mL |
| 7 | MIX 1 2 3 | ANALYTICAL LAB | 11/5/2013 10:18:47 AM | 0.519 | mg/ml | 0.519 | 1.02 | 1 Abs = 1 mg / mL |
| 8 | MIX 1 2 3 | ANALYTICAL LAB | 11/5/2013 10:19:11 AM | 0.733 | mg/ml | 0.733 | 1.00 | 1 Abs = 1 mg / mL |

FIG. 7

| # | SAMPLE ID | USER NAME | DATE AND TIME | PROTEIN CONC | UNIT | A280 | 260/280 | SAMPLE TYPE |
|---|---|---|---|---|---|---|---|---|
| 1 | CONTROL | ANALYTICAL LAB | 11/11/2013 10:25:14 AM | 0.511 | mg/ml | 0.511 | 0.89 | 1 Abs = 1 mg / mL |
| 2 | CONTROL | ANALYTICAL LAB | 11/11/2013 10:25:37 AM | 0.494 | mg/ml | 0.494 | 0.89 | 1 Abs = 1 mg / mL |
| 3 | CONTROL | ANALYTICAL LAB | 11/11/2013 10:25:56 AM | 0.493 | mg/ml | 0.493 | 0.90 | 1 Abs = 1 mg / mL |
| 4 | cm2 | ANALYTICAL LAB | 11/11/2013 10:26:42 AM | 0.709 | mg/ml | 0.709 | 1.02 | 1 Abs = 1 mg / mL |
| 5 | cm2 | ANALYTICAL LAB | 11/11/2013 10:27:05 AM | 0.639 | mg/ml | 0.639 | 0.90 | 1 Abs = 1 mg / mL |
| 6 | cm2 | ANALYTICAL LAB | 11/11/2013 10:27:26 AM | 0.706 | mg/ml | 0.706 | 1.01 | 1 Abs = 1 mg / mL |
| 7 | cm4 | ANALYTICAL LAB | 11/11/2013 10:28:22 AM | 0.682 | mg/ml | 0.682 | 0.95 | 1 Abs = 1 mg / mL |
| 8 | cm4 | ANALYTICAL LAB | 11/11/2013 10:28:50 AM | 0.687 | mg/ml | 0.687 | 0.94 | 1 Abs = 1 mg / mL |
| 9 | cm4 | ANALYTICAL LAB | 11/11/2013 10:29:18 AM | 0.685 | mg/ml | 0.685 | 0.95 | 1 Abs = 1 mg / mL |
| 10 | cm mix 1&2 | ANALYTICAL LAB | 11/11/2013 10:30:26 AM | 0.712 | mg/ml | 0.712 | 1.02 | 1 Abs = 1 mg / mL |
| 11 | cm mix 1&2 | ANALYTICAL LAB | 11/11/2013 10:30:44 AM | 0.721 | mg/ml | 0.721 | 1.03 | 1 Abs = 1 mg / mL |
| 12 | cm mix 1&2 | ANALYTICAL LAB | 11/11/2013 10:31:02 AM | 0.700 | mg/ml | 0.700 | 1.03 | 1 Abs = 1 mg / mL |
| 13 | cm mix 1&2 | ANALYTICAL LAB | 11/11/2013 10:31:20 AM | 0.708 | mg/ml | 0.708 | 1.04 | 1 Abs = 1 mg / mL |
| 14 | cm mix 1&2 | ANALYTICAL LAB | 11/11/2013 10:31:41 AM | 0.709 | mg/ml | 0.709 | 1.03 | 1 Abs = 1 mg / mL |
| 15 | room temp cm1 %2 mix 3 day | ANALYTICAL LAB | 11/11/2013 10:37:03 AM | 0.705 | mg/ml | 0.705 | 1.04 | 1 Abs = 1 mg / mL |
| 16 | room temp cm1 %2 mix 3 day | ANALYTICAL LAB | 11/11/2013 10:37:44 AM | 0.728 | mg/ml | 0.728 | 1.06 | 1 Abs = 1 mg / mL |
| 17 | room temp cm1 %2 mix 3 day | ANALYTICAL LAB | 11/11/2013 10:38:08 AM | 0.713 | mg/ml | 0.713 | 1.05 | 1 Abs = 1 mg / mL |
| 18 | room temp cm1 %2 mix 3 day | ANALYTICAL LAB | 11/11/2013 10:38:35 AM | 0.709 | mg/ml | 0.709 | 1.05 | 1 Abs = 1 mg / mL |

FIG. 8

| # | SAMPLE ID | USER NAME | DATE AND TIME | PROTEIN CONC. | UNIT | A280 | 260/280 | SAMPLE TYPE |
|---|---|---|---|---|---|---|---|---|
| 1 | cm1 | ANALYTICAL LAB | 12/12/2013 11:54:21 AM | 0.582 | mg/ml | 0.582 | 0.98 | 1 Abs = 1 mg / mL |
| 2 | cm1 | ANALYTICAL LAB | 12/12/2013 11:55:30 AM | 0.606 | mg/ml | 0.606 | 0.99 | 1 Abs = 1 mg / mL |
| 3 | cm1 | ANALYTICAL LAB | 12/12/2013 11:56:05 AM | 0.585 | mg/ml | 0.585 | 1.00 | 1 Abs = 1 mg / mL |
| 4 | cm1 | ANALYTICAL LAB | 12/12/2013 11:56:40 AM | 0.587 | mg/ml | 0.587 | 0.98 | 1 Abs = 1 mg / mL |
| 5 | cm2 | ANALYTICAL LAB | 12/12/2013 11:58:29 AM | 0.551 | mg/ml | 0.551 | 0.85 | 1 Abs = 1 mg / mL |
| 6 | cm2 | ANALYTICAL LAB | 12/12/2013 11:59:07 AM | 0.582 | mg/ml | 0.582 | 0.84 | 1 Abs = 1 mg / mL |
| 7 | cm2 | ANALYTICAL LAB | 12/12/2013 11:59:43 AM | 0.556 | mg/ml | 0.556 | 0.85 | 1 Abs = 1 mg / mL |
| 8 | cm2 | ANALYTICAL LAB | 12/12/2013 12:00:14 PM | 0.550 | mg/ml | 0.550 | 0.84 | 1 Abs = 1 mg / mL |
| 9 | cm2 | ANALYTICAL LAB | 12/12/2013 12:00:46 PM | 0.576 | mg/ml | 0.576 | 0.84 | 1 Abs = 1 mg / mL |
| 10 | cm2 | ANALYTICAL LAB | 12/12/2013 12:02:19 PM | 0.077 | mg/ml | 0.077 | 1.07 | 1 Abs = 1 mg / mL |
| 11 | cm3 | ANALYTICAL LAB | 12/12/2013 12:02:33 PM | 0.109 | mg/ml | 0.109 | 1.00 | 1 Abs = 1 mg / mL |
| 12 | cm3 | ANALYTICAL LAB | 12/12/2013 12:03:03 PM | 0.157 | mg/ml | 0.157 | 1.01 | 1 Abs = 1 mg / mL |
| 13 | cm3 | ANALYTICAL LAB | 12/12/2013 12:03:40 PM | 0.176 | mg/ml | 0.176 | 1.02 | 1 Abs = 1 mg / mL |
| 14 | cm3 | ANALYTICAL LAB | 12/12/2013 12:04:14 PM | 0.182 | mg/ml | 0.182 | 0.97 | 1 Abs = 1 mg / mL |
| 15 | cm3 | ANALYTICAL LAB | 12/12/2013 12:06:15 PM | 0.692 | mg/ml | 0.692 | 0.87 | 1 Abs = 1 mg / mL |
| 16 | cm4 | ANALYTICAL LAB | 12/12/2013 12:06:28 PM | 0.694 | mg/ml | 0.694 | 0.88 | 1 Abs = 1 mg / mL |
| 17 | cm4 | ANALYTICAL LAB | 12/12/2013 12:06:55 PM | 0.696 | mg/ml | 0.696 | 0.88 | 1 Abs = 1 mg / mL |
| 18 | cm4 | ANALYTICAL LAB | 12/12/2013 12:07:21 PM | 0.693 | mg/ml | 0.693 | 0.88 | 1 Abs = 1 mg / mL |
| 19 | cm5 | ANALYTICAL LAB | 12/12/2013 12:08:47 PM | 0.558 | mg/ml | 0.558 | 0.98 | 1 Abs = 1 mg / mL |
| 20 | cm5 | ANALYTICAL LAB | 12/12/2013 12:09:20 PM | 0.560 | mg/ml | 0.560 | 0.96 | 1 Abs = 1 mg / mL |
| 21 | cm5 | ANALYTICAL LAB | 12/12/2013 12:09:45 PM | 0.557 | mg/ml | 0.557 | 0.99 | 1 Abs = 1 mg / mL |
| 22 | cm5 | ANALYTICAL LAB | 12/12/2013 12:10:25 PM | -0.019 | mg/ml | -0.019 | 0.68 | 1 Abs = 1 mg / mL |
| 23 | cm6 | ANALYTICAL LAB | 12/12/2013 12:11:43 PM | 0.548 | mg/ml | 0.548 | 0.94 | 1 Abs = 1 mg / mL |
| 24 | cm6 | ANALYTICAL LAB | 12/12/2013 12:12:09 PM | 0.548 | mg/ml | 0.548 | 0.94 | 1 Abs = 1 mg / mL |
| 25 | cm6 | ANALYTICAL LAB | 12/12/2013 12:12:28 PM | 0.556 | mg/ml | 0.556 | 0.92 | 1 Abs = 1 mg / mL |
| 26 | cm7 | ANALYTICAL LAB | 12/12/2013 12:14:01 PM | 0.513 | mg/ml | 0.513 | 1.09 | 1 Abs = 1 mg / mL |
| 27 | cm7 | ANALYTICAL LAB | 12/12/2013 12:14:27 PM | 0.512 | mg/ml | 0.512 | 1.10 | 1 Abs = 1 mg / mL |
| 28 | cm7 | ANALYTICAL LAB | 12/12/2013 12:14:52 PM | 0.514 | mg/ml | 0.514 | 1.09 | 1 Abs = 1 mg / mL |
| 29 | cm7 | ANALYTICAL LAB | 12/12/2013 12:15:42 PM | -0.024 | mg/ml | -0.024 | 0.46 | 1 Abs = 1 mg / mL |
| 30 | cm8 | ANALYTICAL LAB | 12/12/2013 12:16:28 PM | 0.614 | mg/ml | 0.614 | 0.90 | 1 Abs = 1 mg / mL |
| 31 | cm8 | ANALYTICAL LAB | 12/12/2013 12:16:51 PM | 0.616 | mg/ml | 0.616 | 0.92 | 1 Abs = 1 mg / mL |
| 32 | cm8 | ANALYTICAL LAB | 12/12/2013 12:17:11 PM | 0.627 | mg/ml | 0.627 | 0.91 | 1 Abs = 1 mg / mL |
| 33 | cm8 | ANALYTICAL LAB | 12/12/2013 12:17:36 PM | 0.612 | mg/ml | 0.612 | 0.91 | 1 Abs = 1 mg / mL |
| 34 | cm9 | ANALYTICAL LAB | 12/12/2013 12:19:31 PM | 0.520 | mg/ml | 0.520 | 0.96 | 1 Abs = 1 mg / mL |
| 35 | cm9 | ANALYTICAL LAB | 12/12/2013 12:20:00 PM | 0.510 | mg/ml | 0.510 | 0.97 | 1 Abs = 1 mg / mL |

FROM FIG. 9A

| # | SAMPLE ID | USER NAME | DATE AND TIME | PROTEIN CONC. | UNIT | A280 | 260/280 | SAMPLE TYPE |
|---|---|---|---|---|---|---|---|---|
| 36 | cm9 | ANALYTICAL LAB | 12/12/2013 12:20:39 PM | 0.515 | mg/ml | 0.515 | 0.97 | 1 Abs = 1 mg / mL |
| 37 | cm10 | ANALYTICAL LAB | 12/12/2013 12:22:58 PM | 0.600 | mg/ml | 0.600 | 0.94 | 1 Abs = 1 mg / mL |
| 38 | cm10 | ANALYTICAL LAB | 12/12/2013 12:23:20 PM | 0.593 | mg/ml | 0.593 | 0.94 | 1 Abs = 1 mg / mL |
| 39 | cm10 | ANALYTICAL LAB | 12/12/2013 12:23:42 PM | 0.593 | mg/ml | 0.593 | 0.94 | 1 Abs = 1 mg / mL |
| 40 | cm11 | ANALYTICAL LAB | 12/12/2013 12:25:20 PM | 0.601 | mg/ml | 0.601 | 0.92 | 1 Abs = 1 mg / mL |
| 41 | cm11 | ANALYTICAL LAB | 12/12/2013 12:25:45 PM | 0.602 | mg/ml | 0.602 | 0.91 | 1 Abs = 1 mg / mL |
| 42 | cm11 | ANALYTICAL LAB | 12/12/2013 12:26:03 PM | 0.613 | mg/ml | 0.613 | 0.92 | 1 Abs = 1 mg / mL |
| 43 | cm11 | ANALYTICAL LAB | 12/12/2013 12:26:31 PM | 0.608 | mg/ml | 0.608 | 0.92 | 1 Abs = 1 mg / mL |
| 44 | cm12 | ANALYTICAL LAB | 12/12/2013 12:28:15 PM | 0.619 | mg/ml | 0.619 | 0.94 | 1 Abs = 1 mg / mL |
| 45 | cm12 | ANALYTICAL LAB | 12/12/2013 12:28:35 PM | 0.628 | mg/ml | 0.628 | 0.95 | 1 Abs = 1 mg / mL |
| 46 | cm12 | ANALYTICAL LAB | 12/12/2013 12:28:55 PM | 0.629 | mg/ml | 0.629 | 0.95 | 1 Abs = 1 mg / mL |
| 47 | cm13 | ANALYTICAL LAB | 12/12/2013 12:30:22 PM | 0.594 | mg/ml | 0.594 | 0.98 | 1 Abs = 1 mg / mL |
| 48 | cm13 | ANALYTICAL LAB | 12/12/2013 12:30:48 PM | 0.582 | mg/ml | 0.582 | 0.98 | 1 Abs = 1 mg / mL |
| 49 | cm13 | ANALYTICAL LAB | 12/12/2013 12:31:10 PM | 0.587 | mg/ml | 0.587 | 1.00 | 1 Abs = 1 mg / mL |
| 50 | cm13 | ANALYTICAL LAB | 12/12/2013 12:31:27 PM | 0.586 | mg/ml | 0.586 | 0.98 | 1 Abs = 1 mg / mL |
| 51 | cm13 | ANALYTICAL LAB | 12/12/2013 12:33:51 PM | 0.600 | mg/ml | 0.600 | 0.95 | 1 Abs = 1 mg / mL |
| 52 | cm13 | ANALYTICAL LAB | 12/12/2013 12:34:11 PM | 0.589 | mg/ml | 0.589 | 0.96 | 1 Abs = 1 mg / mL |
| 53 | cm13 | ANALYTICAL LAB | 12/12/2013 12:34:35 PM | 0.588 | mg/ml | 0.588 | 0.98 | 1 Abs = 1 mg / mL |
| 54 | cm13 | ANALYTICAL LAB | 12/12/2013 12:34:59 PM | 0.594 | mg/ml | 0.594 | 0.97 | 1 Abs = 1 mg / mL |
| 55 | cm14 | ANALYTICAL LAB | 12/12/2013 12:35:15 PM | 0.599 | mg/ml | 0.599 | 0.97 | 1 Abs = 1 mg / mL |
| 56 | cm14 | ANALYTICAL LAB | 12/12/2013 12:35:33 PM | 0.608 | mg/ml | 0.608 | 0.96 | 1 Abs = 1 mg / mL |
| 57 | cm14 | ANALYTICAL LAB | 12/12/2013 12:35:51 PM | 0.611 | mg/ml | 0.611 | 0.96 | 1 Abs = 1 mg / mL |
| 58 | cm14 | ANALYTICAL LAB | 12/12/2013 12:36:08 PM | 0.605 | mg/ml | 0.605 | 0.96 | 1 Abs = 1 mg / mL |
| 59 | cm15 | ANALYTICAL LAB | 12/12/2013 12:37:25 PM | 0.578 | mg/ml | 0.578 | 0.97 | 1 Abs = 1 mg / mL |
| 60 | cm15 | ANALYTICAL LAB | 12/12/2013 12:37:46 PM | 0.573 | mg/ml | 0.573 | 0.98 | 1 Abs = 1 mg / mL |
| 61 | cm15 | ANALYTICAL LAB | 12/12/2013 12:38:05 PM | 0.585 | mg/ml | 0.585 | 0.97 | 1 Abs = 1 mg / mL |
| 62 | cm15 | ANALYTICAL LAB | 12/12/2013 12:38:23 PM | 0.591 | mg/ml | 0.591 | 0.96 | 1 Abs = 1 mg / mL |
| 63 | cm15 | ANALYTICAL LAB | 12/12/2013 12:38:44 PM | 0.585 | mg/ml | 0.585 | 0.98 | 1 Abs = 1 mg / mL |
| 64 | cm15 | ANALYTICAL LAB | 12/12/2013 12:39:48 PM | 0.619 | mg/ml | 0.619 | 0.92 | 1 Abs = 1 mg / mL |
| 65 | cm15 | ANALYTICAL LAB | 12/12/2013 12:40:10 PM | 0.582 | mg/ml | 0.582 | 0.97 | 1 Abs = 1 mg / mL |
| 66 | cm15 | ANALYTICAL LAB | 12/12/2013 12:40:29 PM | 0.583 | mg/ml | 0.583 | 0.96 | 1 Abs = 1 mg / mL |
| 67 | cm15 | ANALYTICAL LAB | 12/12/2013 12:40:52 PM | 0.586 | mg/ml | 0.586 | 0.95 | 1 Abs = 1 mg / mL |
| 68 | cm17 | ANALYTICAL LAB | 12/12/2013 12:42:59 PM | 0.541 | mg/ml | 0.541 | 0.97 | 1 Abs = 1 mg / mL |
| 69 | cm17 | ANALYTICAL LAB | 12/12/2013 12:43:24 PM | 0.548 | mg/ml | 0.548 | 0.98 | 1 Abs = 1 mg / mL |
| 70 | cm17 | ANALYTICAL LAB | 12/12/2013 12:44:06 PM | 0.546 | mg/ml | 0.546 | 0.98 | 1 Abs = 1 mg / mL |

FROM FIG. 9B

| # | SAMPLE ID | USER NAME | DATE AND TIME | PROTEIN CONC. | UNIT | A280 | 260/280 | SAMPLE TYPE |
|---|-----------|-----------|---------------|---------------|------|------|---------|-------------|
| 71 | cm18 | ANALYTICAL LAB | 12/12/2013 12:44:58 PM | 0.521 | mg/ml | 0.521 | 0.94 | 1 Abs = 1 mg / mL |
| 72 | cm18 | ANALYTICAL LAB | 12/12/2013 12:45:19 PM | 0.518 | mg/ml | 0.518 | 0.95 | 1 Abs = 1 mg / mL |
| 73 | cm18 | ANALYTICAL LAB | 12/12/2013 12:45:40 PM | 0.536 | mg/ml | 0.536 | 0.94 | 1 Abs = 1 mg / mL |
| 74 | cm18 | ANALYTICAL LAB | 12/12/2013 12:46:09 PM | 0.523 | mg/ml | 0.523 | 0.96 | 1 Abs = 1 mg / mL |
| 75 | cm18 | ANALYTICAL LAB | 12/12/2013 12:46:16 PM | 0.520 | mg/ml | 0.520 | 0.95 | 1 Abs = 1 mg / mL |
| 76 | cm19 | ANALYTICAL LAB | 12/12/2013 12:47:27 PM | 0.597 | mg/ml | 0.597 | 0.93 | 1 Abs = 1 mg / mL |
| 77 | cm19 | ANALYTICAL LAB | 12/12/2013 12:47:45 PM | 0.595 | mg/ml | 0.595 | 0.95 | 1 Abs = 1 mg / mL |
| 78 | cm19 | ANALYTICAL LAB | 12/12/2013 12:48:03 PM | 0.597 | mg/ml | 0.597 | 0.96 | 1 Abs = 1 mg / mL |
| 79 | cm20 | ANALYTICAL LAB | 12/12/2013 12:49:17 PM | 0.673 | mg/ml | 0.673 | 0.89 | 1 Abs = 1 mg / mL |
| 80 | cm20 | ANALYTICAL LAB | 12/12/2013 12:49:39 PM | 0.692 | mg/ml | 0.692 | 0.88 | 1 Abs = 1 mg / mL |
| 81 | cm20 | ANALYTICAL LAB | 12/12/2013 12:49:58 PM | 0.685 | mg/ml | 0.685 | 0.89 | 1 Abs = 1 mg / mL |
| 82 | cm20 | ANALYTICAL LAB | 12/12/2013 12:50:05 PM | 0.671 | mg/ml | 0.671 | 0.90 | 1 Abs = 1 mg / mL |
| 83 | cm20 | ANALYTICAL LAB | 12/12/2013 12:50:11 PM | 0.688 | mg/ml | 0.688 | 0.90 | 1 Abs = 1 mg / mL |

FIG. 9C

BLACK - ADD MEDIA
WHITE - ADD NOTHING
RED - 70ug = 100ul OF MIX
ORANGE - 60ug = 86ul OF MIX
YELLOW - 50ug = 71ul
GREEN - 40ug = 57ul
BLUE - 30ug = 43ul
PURPLE - 20ug = 29ul
HOT PINK - 10ug = 14ul
LIME GREEN - 5ug = 7ul
BROWN - 1ug = 1.4ul
GREY - 0.7ug = 1ul

TO FIG 13B

FROM FIG. 13A

| | | | | | |
|---|---|---|---|---|---|
| 10 ug | B7 | 7 | 0.074 | 0.095 | 0.054932 |
| | C7 | | 0.066 | | |
| | D7 | | 0.075 | | |
| | E7 | | 0.193 | | |
| | F7 | | 0.067 | | |
| 5 ug | B8 | 8 | 0.082 | 0.081 | 0.002683 |
| | C8 | | 0.082 | | |
| | D8 | | 0.079 | | |
| | E8 | | 0.082 | | |
| 1 ug | B9 | 9 | 0.076 | 0.075 | 0.014822 |
| | C9 | | 0.069 | | |
| | D9 | | 0.072 | | |
| | E9 | | 0.083 | | |
| 0.7 ug | B10 | 10 | 0.106 | 0.09 | 0.013353 |
| | C10 | | 0.094 | | |
| | D10 | | 0.087 | | |
| | E10 | | 0.071 | | |
| CONTROL | B11 | 11 | 0.099 | 0.0646 | 0.015547 |
| | B12 | | 0.066 | | |
| | C11 | | 0.063 | | |
| | C12 | | 0.072 | | |
| | D11 | | 0.061 | | |
| | D12 | | 0.061 | | |
| | E11 | | 0.123 | | |

FIG. 13B

COSMETIC COMPOSITIONS AND METHOD OF MAKING THE SAME

CROSS REFERENCE TO RELATED APPLICATIONS

This application claims priority to U.S. Provisional Patent Application Ser. No. 61/927,674 filed Jan. 15, 2014. The disclosure of U.S. Provisional Patent Application 61/927,674 is incorporated by reference herein in its entirety.

FIELD

The present invention generally relates to cosmetic and dermatological compositions and preparations comprising serum derived from cultured neonatal human skin cells, in particular, keratinocytes and fibroblasts. The invention also relates to methods for treating topical burns, wounds, or scars using said compositions. The invention, furthermore, relates to a method for preventing and/or combating cutaneous signs of aging and for protecting the skin against the harmful effects caused by UV radiation. Finally the invention relates to a method of producing a serum useful in the serum derived cosmetic compositions through novel cell culture techniques.

BACKGROUND

Wound healing is a complex process. In normal skin, the epidermis and dermis exists in steady state equilibrium, forming a barrier against the external environment. Normal wound healing processes can be classified into three stages namely the inflammatory, proliferative and maturation phases. The inflammatory phase typically lasts 0-2 days and involves an orderly recruitment of cells to the wound area. This is followed by the 2-6 day proliferative phase, in which fibroblasts, keratinocytes and other cells in the wound bed begin to actively proliferate to close the wound. During the first phase of tissue repair, an acute inflammatory response with cellular migration occurs. Neutrophils predominate for the first 24-48 hours and macrophages become active by the third day. The neutrophils and macrophages phagocytose and digest pathologic organisms and tissue debris. The maturation phase follows the proliferative phase, peaking at 21 days.

Growth factors are known to play an important role in the wound healing process and are involved in a number of critical cellular processes including cell proliferation, adhesion, morphologic appearance, differentiation, migration, inflammatory responses, angiogenesis, and cell death.

Under appropriate conditions, fibroblasts secret collagens, glycosaminoglycans, reticular and elastic fibers, glycoproteins found in the extracellular matrix and cytokine thymic stromal lymphoprotein or cytokine TSLP which are beneficial to wound or burn treatment. It has been shown that tissue damage stimulates fibrocytes and inducing cellular division. Fibroblasts synthesize the extracellular matrix and collagen in animal tissues and play a critical role in wound healing. Keratinocytes constitute 90% of the cells found in the epidermis. The primary function of keratinocytes is the formation of a barrier against environmental damage such as pathogens (bacteria, fungi, parasites, viruses), heat, UV radiation and water loss. Once pathogens start to invade the upper layers of the epidermis, keratinocytes react with the production of proinflammatory mediators and in particular chemokines such as CXCL10, CCL2 which attract leukocytes to the site of pathogen invasion.

There are currently no dermatologic or cosmetic compositions whereby cell culture conditions yield a cellular population predominated by keratinocytes and fibroblasts that secrete such high concentrations of beneficial proteins and other compounds with therapeutic properties.

SUMMARY

One object of the present invention is to provide dermatological and/or cosmetic compositions or preparations useful in the treatment of cutaneous wounds, burns, scars or cutaneous signs of aging, such as wrinkles. In one embodiment, the compositions comprise serum or conditioned media generated from cultured keratinocyte and fibroblast cell types exclusively. The serum derived from the cultured keratinocytes and fibroblasts comprises proteins and other compounds secreted by keratinocytes and fibroblasts in culture with therapeutic properties. In some embodiments, said preparations contain additional agents and may include a pharmaceutical medium to carry the collected serum such as an aqueous solution, suspension, dispersion, salve, ointment, gel, cream, lotion, spray or paste.

In one embodiment, said compositions include serum or conditioned media generated by culturing keratinocytes and fibroblasts exclusively in combination and extracting conditioned media from said combined cultures of keratinocytes and fibroblasts. In other embodiments, said compositions include serum generated by culturing keratinocytes and fibroblasts separately, extracting conditioned media from said cultures, and combining the collected serum for use in the composition.

In some embodiments, the serum is derived from cultured keratinocytes and fibroblasts obtained from epithelial cells isolated from human neonatal foreskin. In another embodiment, the serum is derived from cultured keratinocytes and fibroblasts grown in minimum essential media. In yet another embodiment, the cells are cultured in minimum essential media at times with and at times without the addition of exogenous growth factors. In yet another embodiment, the cells are cultured in minimum essential media without the addition of phenol, bovine, or porcine derived agents. In some embodiments, the serum comprises proteins secreted from keratinocytes and fibroblasts that have been cultured in minimum essential media without exogenous growth factors, phenol, bovine derived agents, or porcine derived agents.

Another object of the present invention is to provide a method of producing a serum or conditioned media for use in cosmetic compositions or preparations. In some embodiments, the steps associated with said method comprise harvesting epithelial cells from neonatal foreskin, culturing the epithelial cells in a culture container containing a predetermined volume of media with growth factor but without porcine or bovine product until keratinocytes and fibroblasts predominate in culture in substantially equal proportions and the culture reaches at least about 80 percent confluence. The method may additional comprise the step of removing the media from the container and washing the suspended cells with buffer, adding a predetermined volume of sterile media to the culture container without growth factor and without porcine and or bovine product and culturing the cells a second time, monitoring the cell culture for contamination, extracting a predetermined volume of conditioned media from the cell culture after a predetermined time period and replacing this volume with an equal volume of sterile media, and repeating the extraction and replacement steps until growth factor concentrations are optimized. In some embodiments, following initial growth and combined culturing methodologies, the keratinocytes and fibroblasts are separated and independently grown in culture generating serums that are combined and used in the preparation.

Another object of the present invention is a method of treating burns, wounds, scars, and signs of aging, such as wrinkles using the compositions and preparations described above.

BRIEF DESCRIPTION OF THE DRAWINGS

Representative embodiments of the invention are disclosed in more detail with reference to the following figures.

FIG. 1A-C is a table with data from a NanoDrop 2000 Analysis of various samples of the serum derived from cultured keratinocytes and fibroblasts.

FIG. 2 is a table with data from a NanoDrop 2000 Analysis of various samples of the serum derived from cultured keratinocytes and fibroblasts.

FIG. 3 is a table with data from as NanoDrop 2000 Analysis of various samples of the serum derived from cultured keratinocytes and fibroblasts.

FIG. 4 is a table with data from a NanoDrop 2000 Analysis of various samples of the serum derived from cultured keratinocytes and fibroblasts.

FIG. 5 is a table with data from a NanoDrop 2000 Analysis of various samples of the serum derived from cultured keratinocytes and fibroblasts.

FIG. 6 is a table with data from a NanoDrop 2000 Analysis of various samples of the serum derived from cultured keratinocytes and fibroblasts.

FIG. 7 is a table with data from a NanoDrop 2000 Analysis of various sample of the serum derived from cultured keratinocytes and fibroblasts.

FIG. 8 is a table with data from a NanoDrop 2000 Analysis of various samples of the serum derived from cultured keratinocytes and fibroblasts.

FIG. 9A-C is a table with data from a NanoDrop 2000 Analysis of various samples of the serum derived from cultured keratinocytes and fibroblasts.

FIG. 13A-B is the raw data and a bar graph showing the improvement in cell viability with increased protein concentration in the MTT assay.

DETAILED DESCRIPTION

Figure 10:
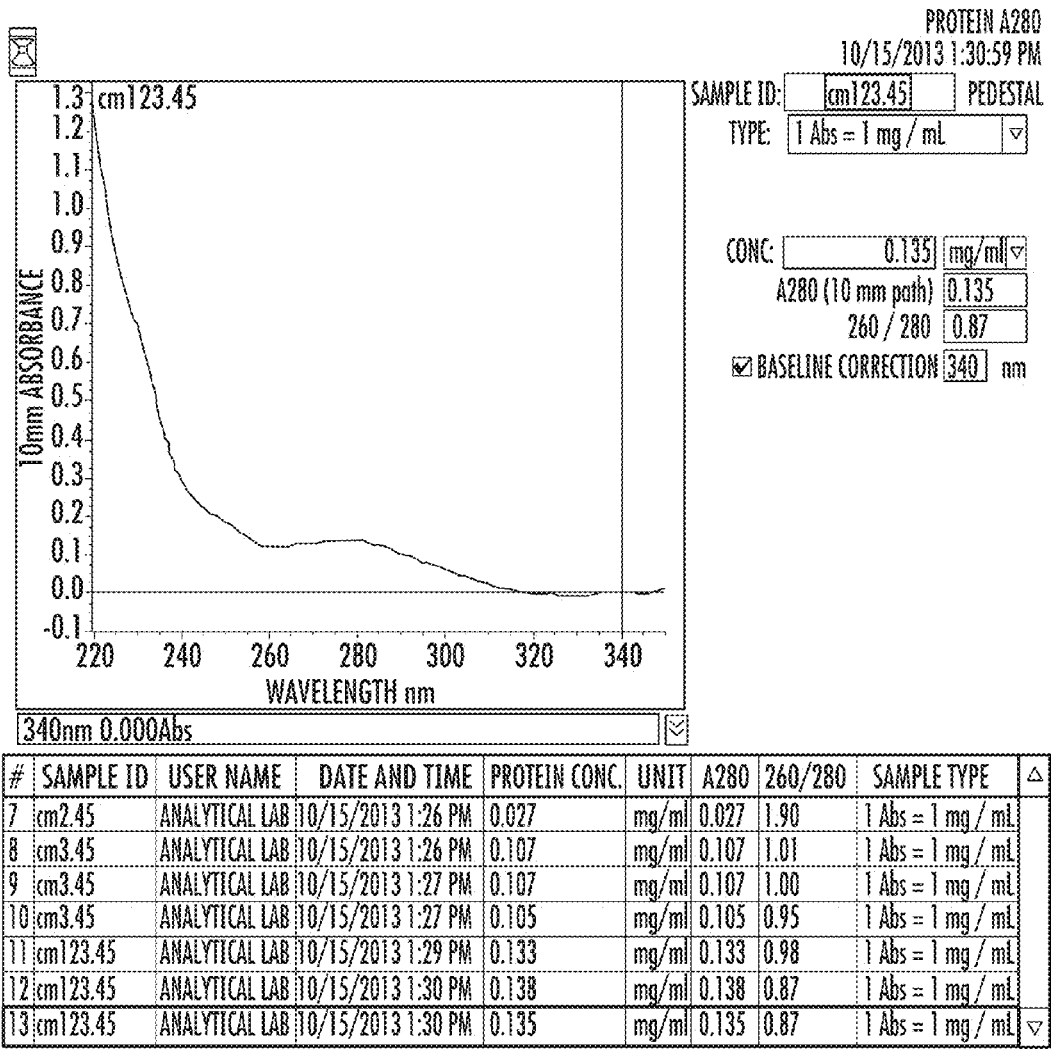
FIG. 10 is a graphical representation of a NanoDrop 2000 Analysis of a concentrated combined serum sample.
Figure 11:
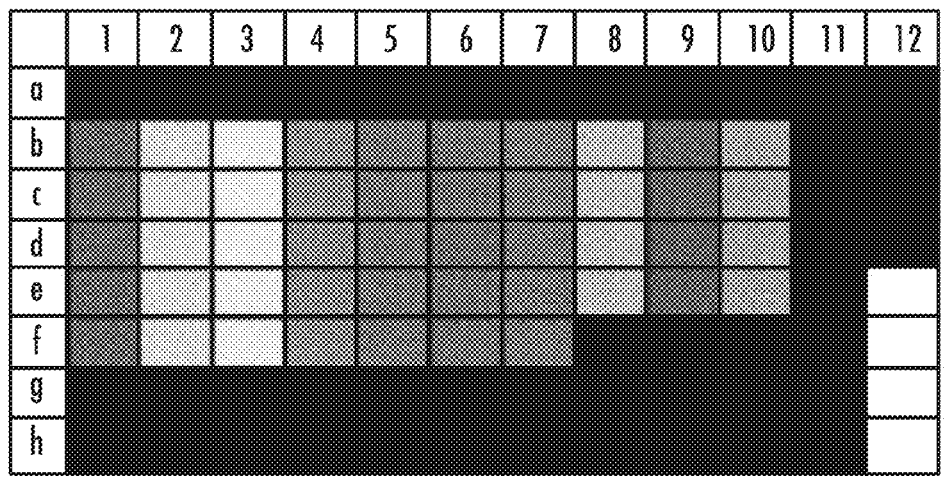
FIG. 11 is a table showing the various protein concentrations used in the MIT 3-(4,5-dimethylthiazol-2-yl)-2,5-diphenyltetrazolium bromide) assay.

The present invention now will be described more fully hereinafter with reference to the accompanying drawings, which form a part hereof, and which show, by way of illustration, specific exemplary embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as methods or compositions.

It should be noted that although the discussions herein may refer to a specific order and composition of method steps, it is understood that the order of these steps may differ from what is described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present invention.

Throughout the specification and claims, the following terms take the meanings explicitly associated herein, unless the context clearly dictates otherwise. The phrase "in one embodiment" or "in some embodiments" or "in a preferred embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

The serum, keratinocyte fibroblast serum ("KFS"), is a combination of both conditioned media and serum isolated from culturing keratinocyte and fibroblast cell types. In some embodiments, keratinocytes and fibroblasts are cultured exclusively either in combination or independently in separate cultures and subsequently combined post extraction procedure. In some embodiments, the compositions include anti-aging creams or wrinkle creams which enhance skin texture and tone. In said embodiments, the cream can be applied to neck and face during morning and evening after cleaning and toning the skin. Other applications in wound treatment and care, burn treatment and care, scar treatment and care, and cosmetic applications are also contemplated and covered herein. In some embodiments, the compositions contain an FDA hypoallergenic base in addition to Vitamin A, Vitamin C and growth factors found in the conditioned media.

The compositions according to the invention are preferably present in a form adapted for topical application comprising a cosmetically or dermatologically acceptable medium. "Cosmetically or dermatologically acceptable" means media which are suitable for a use in which they come into contact with the skin or human skin appendages without posing a risk of toxicity, intolerance, instability, allergic reaction, etc.

In accordance with yet further advantageous embodiment, the compositions may include an active ingredient that may be in solid form which is previously solubilized in a cosmetic or pharmaceutical vector such as liposomes, or adsorbed on pulverulent organic polymers, mineral supports such as talcs and betonites, and more generally solubilized in, or fixed on, any physiologically acceptable vector.

The compositions to be applied to the skin may be present in the form of aqueous or hydroalcoholic solution, an oil-in-water or water-in-oil emulsion, a microemulsion, acqueous or anhydrous gels, serum, or else a dispersion of vesicles, a patch, cream, spray, salve, ointment, lotions, gels solution, suspension, etc.

In a specific embodiment the composition according to the invention also contains at least one further active ingredient which promotes the action of said peptide active ingredient. Non-limiting examples include the following classes of ingredients: other peptide active ingredients, vegetable extracts, healing agents, anti-age agents, anti-wrinkle agents, soothing agents, anti-radical agents, anti-UV agents, agents stimulating the synthesis of dermal macromolecules or the energy metabolism, hydrating agents, anti-bacterial agents, anti-fungal agents, anti-inflammatory agents, anaesthetic agents, agents modulating cutaneous differentiation, pigmentation or depigmentation, agents stimulating, nail or hair growth, etc. An anti-radical or anti-oxidant agent or an agent stimulating the synthesis of dermal macromolecules, or else an agent stimulating the energy metabolism is preferably used.

Furthermore, additives such as thickening, emulsifying, humectant and emollient agents, perfumes, anti-oxidants, filomogenic agents, chelating agents, sequestering agents, conditioning agents, etc. can be added to the composition.

Numerous vehicles for topical application of dermatological or cosmetic compositions are known in the art. See, e.g., Remington's Pharmaceutical Sciences, Gennaro, A. R., ed., 20th edition, 2000: Williams and Wilkins PA, USA. All compositions usually employed for topically administering pharmaceutical and cosmetic compositions may be used, e.g. creams, lotions, gels, dressings, shampoos, tinctures, pastes, serums, ointments, salves, powders, liquid or semi-liquid formulation, patches, liposomal preparations, solutions, suspensions, liposome suspensions, W/O or O/W emulsions, pomades and pastes and the like as long as the active ingredient is stabilized. Application of said compositions may, if appropriate, be by aerosol e.g. with a propellant such as nitrogen carbon dioxide, a freon, or without a propellant such as a pump spray, drops, lotions, or a semisolid such as a thickened composition which can be applied by a swab. In particular compositions, semisolid compositions such as salves, creams, lotions, pastes, gels, ointments and the like will conveniently be used.

The compositions may be provided for parenteral, systemic or local use, comprising solutions, suspensions, liposome suspensions, W/O (water/oil) or O/W (oil/water) emulsions. In some embodiments the active substance is formulated in a lyophilized form, mixed to suitable lyophilization additives and ready to be redissolved with therapeutically acceptable diluents. Useful lyophilization additives are: buffers, polysaccharides, sucrose, mannitol, inositol, polypeptides, amino acids and any other additive compatible with the active substance. In further embodiments the active substance may be dissolved in phosphate buffer (NaH2PO4/H2O—Na2HPO4/2H2O) in an amount such that the post-lyophilization growth factor/phosphate ratio is comprised between 1:1 and 1:2. Diluents suitable for parenteral use may be: water, physiological solutions, sugar solutions, hydroalcoholic solutions, oily diluents, polyols, like glycerol, ethylene or propylene glycol, or any other diluent compatible with the administration method as for sterility, pH, ionic strength and viscosity.

The vehicle of topical application is a formulation that may be naturally anti-bacterial without any non-natural preservative or anti-microbial agent. It is desirable to minimize the ingredients in order to eliminate complex ingredients that may act as allergenics and/or irritants. The formulations should also ensure long term stability of the active ingredients, preferably providing long shelf life such as One year or longer at room temperature storage.

In some embodiments the active compound may be added to a formulation suitable for topical application containing one or more of glycerol, a salt such as but not limited to sodium chloride, potassium chloride and calcium chloride, purified water, and ethanol. Such compositions are may stabilize the active ingredient represented by the growth factor in the serum. The formulation may be antibacterial by nature and therefore particularly suitable as a topical formulation for dermatological use. The composition of the invention may furthermore comprise an optional additive such as hyaluronic acid (hyalorunate).

In the case of emulsions or suspensions, the composition may contain suitable surfactants of non-ionic, zwitterionic, anionic or cathionic type commonly used in the formulation of medicaments. Oil/water (O/W) hydrophilic emulsions are preferable for parenteral systemic use, whereas water/oil (W/O) lipophilic emulsions are preferable for local or topical use.

Moreover, the compositions of the invention may contain optional additives like isotonic agents, such as sugars or polyalcohols, buffers, chelating agents, antioxidants, antibacterials.

Liquid forms according to the invention can comprise solutions or lotions. These may be aqueous, hydroalcoholic, like ethanol/water, or alcoholic and are obtained by solubilizing the lyophilized substance.

Alternatively, active substance solutions, may be formulated as a gel by addition of known gelling agents, like: starch, glycerin, polyethylene or polypropylene glycol, poly(meth)acrylate, isopropyl alcohol, and hydroxystearate.

Other types of compositions for topical use are emulsions or suspensions in form of pomades, pastes, creams. Examples of lipophilic excipients are: liquid paraffin, anhydrous lanolin, white vaseline, cetyl alcohol, stearyl alcohol, vegetable oils, mineral oils. Agents increasing cutaneous permeability, thereby facilitating the absorption, may advantageously be used. Examples of such agents are physiologically acceptable additives like polyvinyl alcohol, polyethylenglycol (PEG) or dimethylsulfoxide (DMSO).

Other additives used in the topic compositions are isotonic agents, like sugars or polyalcohols, buffers, chelating agents, antioxidants, antibacterials, thickeners, dispersants.

It follows that the preparations may further contain conventional components usually employed in preparations described herein, including oils, fats, waxes, surfactants, humectants, thickening agents, antioxidants, viscosity stabilizers, chelating agents, buffers, preservatives, perfumes, dyestuffs, lower alkanols, and the like.

Delayed-release compositions for local or systemic use may be useful, and comprise polymers like polylactate, poly(meth)acrylate, polyvinylpyrrolidone, methylcellulose carboxymethylcellulose and other substances known in the art. Delayed-release compositions in form of subcutaneous implants based on, e.g. polylactate or other biodegradable polymers may be useful as well.

Though the active substance may be packaged in lyophilized form, the pharmaceutical compositions may also comprise substances stabilizing the growth factor in the active form. Such stabilizers inhibit the formation of intermolecular disulfide bonds, thereby preventing the polymerization of the active substance. However, the amount of stabilizer should be carefully measured in order to concomitantly prevent the reduction of activity. Examples of such substances are: Cystein, Cysteamine, or glutathione in reduced form.

Non-limiting examples of oils include fats and oils such as olive oil and hydrogenated oils; waxes such as beeswax and lanolin; hydrocarbons such as liquid paraffin, ceresin, and squalene; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium steatite, sodium cetylsulfate, polyoxyethylene laurylether phosphate, sodium N-acyl glutamate; cationic surfactants such as stearyldimethylbenzylaminonium chloride and stearyltrimethylammonium chloride; ampholytic surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants include butylated hydroxytoluene, butylated hydroxyanisole, propyl gallate, citric acid and ethoxyquin; examples of chelating agents include disodium edetate and ethanehydroxy diphosphate; examples of buffers include citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid. These substances are merely exemplary, and those of skill in the art will recognize that other substances may be substituted with no loss of functionality.

Generally, and in some embodiments, epithelial cells may be collected from neonatal foreskin and mechanically processed as described below. In some embodiments, cells may be cultured without porcine insulin, phenol (a dye found in media to indicate pH changes and a potential human allergen) or fetal bovine serum for human use standards. It has been noticed that under the culture conditions described herein two cell populations are selected and predominate—keratinocytes and fibroblasts. The active substance, serum, or conditioned media is derived from said keratinocytes and fibroblasts cultured. In a preferred embodiment, the cell culture substantially excludes other cell types other than keratinocytes and fibroblasts. In another preferred embodiment, the keratinocytes and fibroblasts are cultured in combination. And in yet another preferred embodiment, the keratinocytes and fibroblasts are cultured independently—in separate cultures. In some embodiments, in order to generate the desired serum, the cells may be cultured in media (Minimum Essential Media or MEM) without any growth factors. The media was conditioned in such a manner to determine whether naturally secreted growth factors would preserve cell vitality.

In one embodiment, skin cells are isolated from neonatal foreskin retrieved from circumcision after acquiring informed consent from parents. The samples may be temporarily stored, for example, in a sterile 50 milliliter Falcon tube with 5 milliliter of sterile media. In this embodiment, the foreskin samples are ringlets approximately 2-2.5 centimeters in diameter at the internal ring. In the current embodiment, using a 12 blade scalpel, an incision was made in north and south poles on the inner side of the ring. Incisions may be further extended through the entire internal ring (360°) exposing the internal skin tissue. Two skin layers are butterflied creating, a flap and cells were harvested from the exposed area.

To ensure colony establishment and adherence, initially the cells may be grown in MEM with growth factors added such as, for example, L-Glutamine, hydrocortisone hemisuccinate, linoleic acid, Lecithin, HSA, rh FGF β, rh EGF/TGF β-1, rh-insulin, and Ascorbic acid. It has been noted that under these growth conditions two cell types are selected producing a cell culture with about 100 percent keratinocytes and fibroblasts—each making up about 50% of the total cell population. Once the cells reach a certain stage of growth and vitality (represented in this embodiment by 80-100% confluency), the cells may be treated and transferred to MEM or another suitable cell culture media without growth factors to deprive them of certain nutrients and force endogenous metabolism and secretion of growth factor from the cells themselves.

For example, in one embodiment, when the cell culture container (e.g., plates) reach about 80-100% confluency, the plates may be washed with 10 ml of phosphate buffer saline (PBS) three times before the culture/extraction process begins which helps to ensure that most if not all of the compounds (e.g. proteins or growth factors) found in the serum are secreted by the cells themselves and not from an external source. Once washed, fresh sterile media, for example, 10 ml of MEM (minus growth factors, phenol, and bovine or porcine products), may be added. The cells are then incubated and checked daily for infections or contaminants. For example, in one embodiment, cells are extracted using only mechanical means with no proteins (e.g. growth factors) added to the media. Cells are grown in MEM that does not include phenol, porcine (e.g. porcine insulin), or bovine (e.g. FBS) products to preserve human applications.

In one embodiment, after three days of incubation, 5 ml of sample serum is collected from each plate and properly labeled. This process may be repeated multiple times, for example, three more times to yield three more serum samples. In some embodiments, the samples are filtered immediately after collection using a micro filter, preferably a 0.22 or 0.45 micro filter, and even more preferably a 0.45 micro filter.

In another embodiment, following the initial combined culturing protocol wherein fibroblasts and keratinocytes are cultured together to promote growth and adherence, the fibroblasts and keratinocytes are separated via selective media and cultured independently. Conditioned media is extracted from each culture and, in some embodiments, combined to generate the final serum product. For example, once the original cell culture comprising both cell types reaches at least about 80 percent confluence a predetermined volume (e.g., 5 ml) of PBS is placed in the cell culture container, for example a plate or dish, containing both cell lines for a short period (e.g., approximately 30 seconds) and then removed. Next, accutase (e.g., 3 ml) or some other suitable cell detachment solution may be added to the cell culture container after the removal of PBS followed by a short incubation period (e.g., for 5-10 minutes). The cells are checked frequently (e.g., every 3 minutes) and, in some embodiments, the plates are tapped gently to increase cell separation. Cells are now visible on the media surface via microscope.

A predetermined volume of the cell culture solution (e.g., 1.5 ml) may then be added to another cell culture container containing Minimum Essential Media and keratinocyte specific factors, including for example, BPE, rh TGFa, LGlutamine, Hydrocortisone Hemisuccinate, rh Insulin, Epinephrine, and ApoTransferrin. The cells are cultured in this media until keratinocytes predominate, then it is switched back to the original media and growth factors. It was observed that the media used initially for the processing of the foreskin allows the culture of both cell lines simultaneously during the first and second passage yet after the cells are split these cells with the enzyme accutase a couple times the media starts being fibroblast selective and will select fibroblast growth over keratinocytes. Once a culture of keratinocytes is established, it can be grown successfully in the original media. The other 1.5 ml of cell suspension was placed in a 10 ml cell culture dish and added 10 ml of our original media and growth factors, the cells were cultured until only fibroblasts were present.

In some embodiments, after 80 percent confluence is reached the process of serum extraction begins for both cell lines separately. For example, once the cells reach 80-100% confluence in the culture dish the media may be removed and the plate washed 3 times with solution, for example phosphate buffered saline or PBS. Then 10 ml of sterile MEM is added to each plate which are placed in an incubator and monitored frequently for contaminates. On the third day, 5 ml of the serum is collected from each culture and a fresh 5 ml of sterile MEM is added to the plate. No phenol or growth factors are used in this process. This process was repeated three more times generating four serum samples total. Each sample was filtered using a 0.45-micron filter. The samples were labeled (CM1, CM2, CM3, and CM4) and made ready for testing. Once the serum is collected separately for both cell lines 50% of keratinocyte media is added to 50% of fibroblast-conditioned media for the final product.

EXAMPLE 1

Methods and Procedures

Processes were carried out under sterile conditions and applying aseptic technique.
A. Cell Collection and Preparation
A neonatal foreskin specimen was received in a sterile 50 ml falcon tube with 5 ml of sterile media. The vial was opened and media emptied and tissue sample placed on an empty plate. Using a size 12 scalpel blade, two incisions were made on the internal ring of skin—one incision at 12 o'clock and one 6 o'clock. Using a sterile surgical clamp and a size 12 scalpel blade the incision was extended 360 degrees through the internal ring. Another incision at the 12 and 6 o'clock position was made creating two pieces of skin. Using a clamp, each piece of skin was spread open exposing the internal contents of skin. With a size 10 scalpel blade, the internal skin tissue from the sample was scraped and a soup of cells collected. The collected cells were added to a 15 ml falcon tube in 5 ml of media and centrifuged for 5 minutes at 500 rpm. After centrifugation all media was removed and the collected cells were plated in cell culture plates with 10 ml of MEM with, for example, L-glutamine (7.5 mM), hydrocortisone hemisuccinate (1 ug/mL), linoleic acid (0.6 mM), Lecithin (0.6 ug/mL), HAS (500 ug/mL), rh FGF β (5 ng/mL), rh EGF/TGF β-1 (5 ng/mL), rh-insulin (5 ug/mL), and Ascorbic acid (50 ug/mL). Media was changed every three days.
B. Serum Collection
Once the cells were 80-100% confluent in the culture dish all media was removed and the plate was washed 3 times with PBS. 10 ml of sterile MEM without growth factor, phenol, or porcine and bovine product was added to each plate which were placed in an incubator and monitored daily for contaminates. On the third day, 5 ml of the serum was collected and a fresh 5 ml of sterile MEM without growth factor, phenol, or porcine and bovine product was added to the plate. Again, no phenol and or growth factors were used in this process. This process was repeated three more times generating four serum samples total. Each sample was filtered using a 0.45 micron filter. The samples were labeled (CM1, CM2, CM3, and CM4) and made ready for testing.
C. Testing and Analysis
a. NanoDrop 2000 Analysis—Total Protein Concentration
Serum samples CM 1, 2, 3 and 4 were analyzed using a NanoDrop 200 spectrophotometer. The procedure was used to determine total protein concentrations of the conditioned media which helped calculate proper sample load needed for other experiments including the SDS-PAGE assay and the MTT assay. As reflected in FIGS. 1-10, in general, protein concentrations for all four samples were high and demonstrated stability over the test time duration for each sample. It was observed, however, that the protein concentration for CM 4 was generally lower than the other three. This may be in part due to the metabolic stress on the cells after four successive conditioning rounds and incubation. For example, as shown in FIGS. 1 and 3, CM 4 demonstrates lower protein concentrations than the other samples CM 2 and CM 3.

As seen in FIGS. 1-10, the results showed significant and consistent protein concentration among all samples even when filtered using a 0.45 micron filter. Mixed samples (e.g. CM 123) also showed positive results. A mixed sample (CM 123) was exposed to ambient conditions (room temperature, air) and the protein content of the mixed sample was measured using the NanoDrop machine. Taken to ether, the results demonstrated in FIGS. 1-10 confirm protein stability over a substantial period of time.
b. MTT Assay
The MTT (3-(4,5-dimethylthiazol-2-yl)-2,5-diphenyltetrazolium bromide) assay is a colorimetric assay for assessing cell viability through the active mitochondria's NAD(P)H-dependent cellular oxidoreductase enzymes. These enzymes reduce the tetrazolium dye MTT, which is yellow in color, to formazan crystals, which has a purple color. The assay determines mitochondrial activity which, for most cell populations, is related to the number of viable cells. In this case, the assay was done to determine if the condition media (i.e. serum) increased the amount of cells compared to just regular media and how much condition media was needed for growth.

Figure 12:
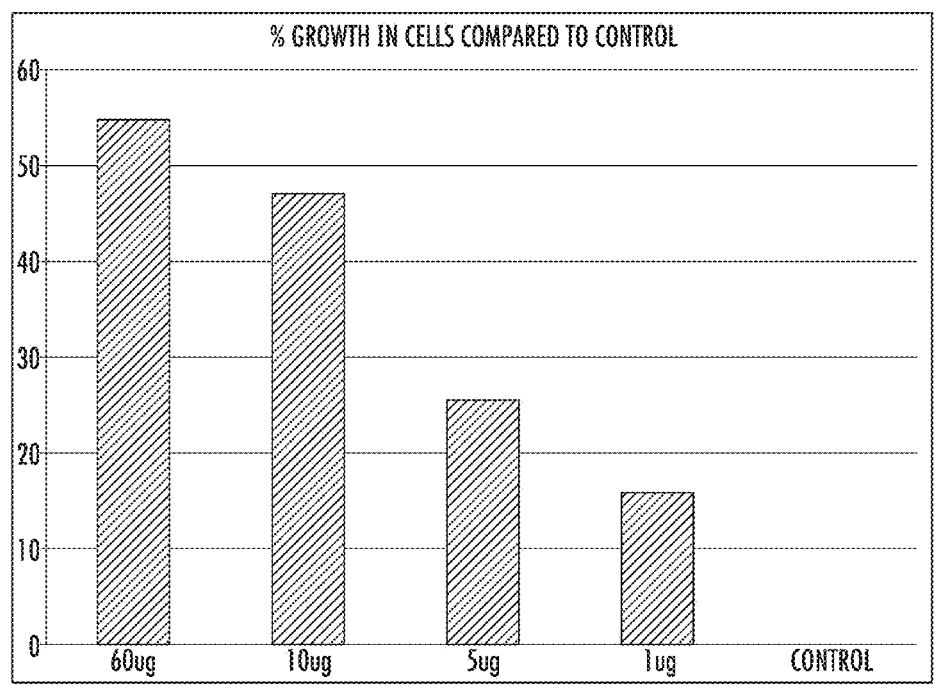
FIG. 12 is a bar graph showing the improvement in cell viability with increased protein concentration in the MTT assay.
Figure 13A:
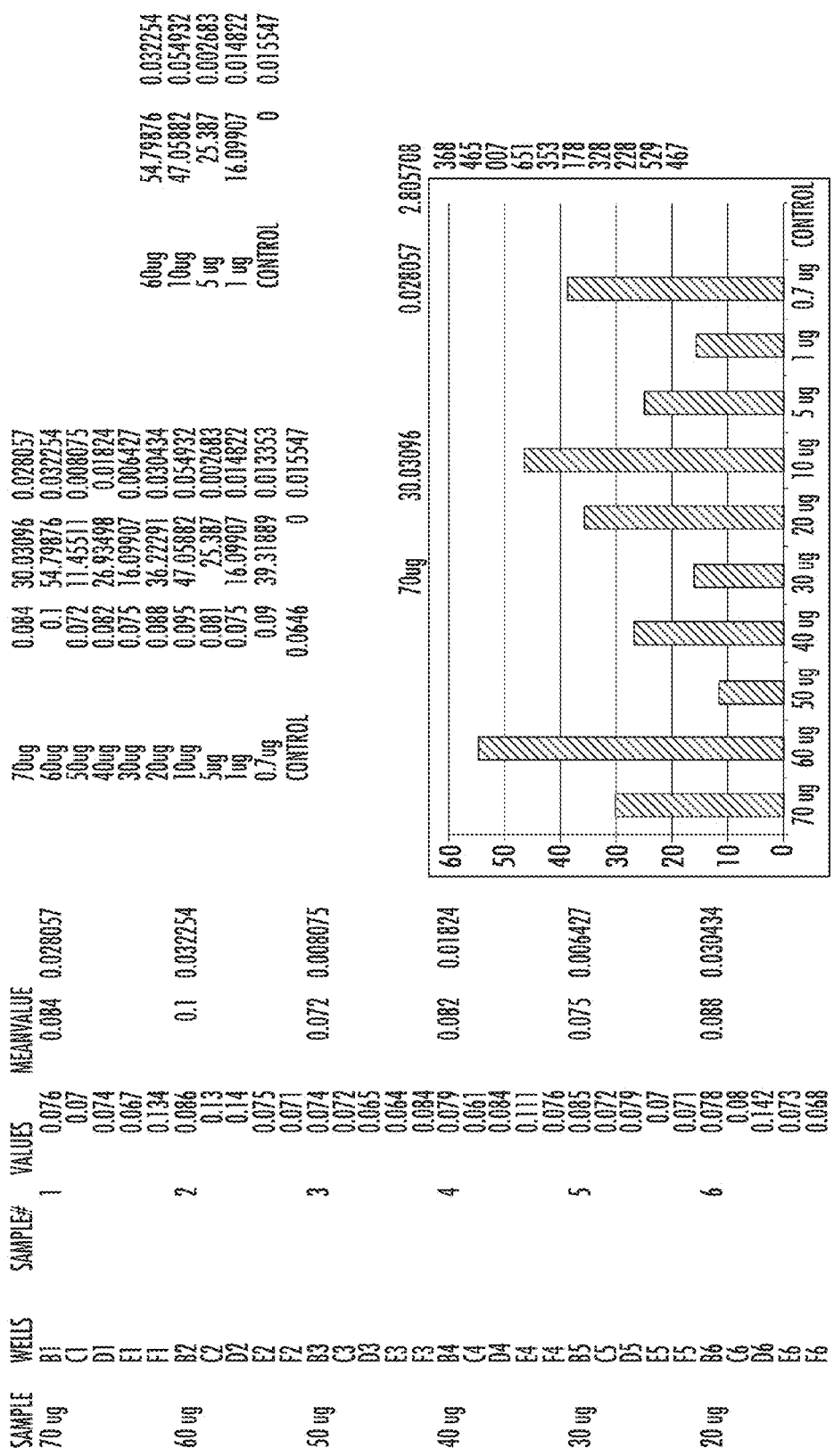

An even amount of keratinocyte cells (5000) were plated in each well of a 96 well plate. The cells were allowed to attach to the plate overnight with normal media. The next day varying amounts of conditioned media (from a filtered sample) were added based on the amount of protein in ug/ml. After 24 hrs of incubation in the new media the cells were tested. The assay demonstrated that cell growth increased with and was directly related to the amount of protein added to the cells. For example, as shown in FIGS. 12-13, at 60 ug the keratinocytes experienced approximately 55% more growth than unconditioned media and at 10 ug the cells experienced approximately 47% more growth than unconditioned media.

c. SDS-PAGE and Mass Spectrometry

Figure 14:
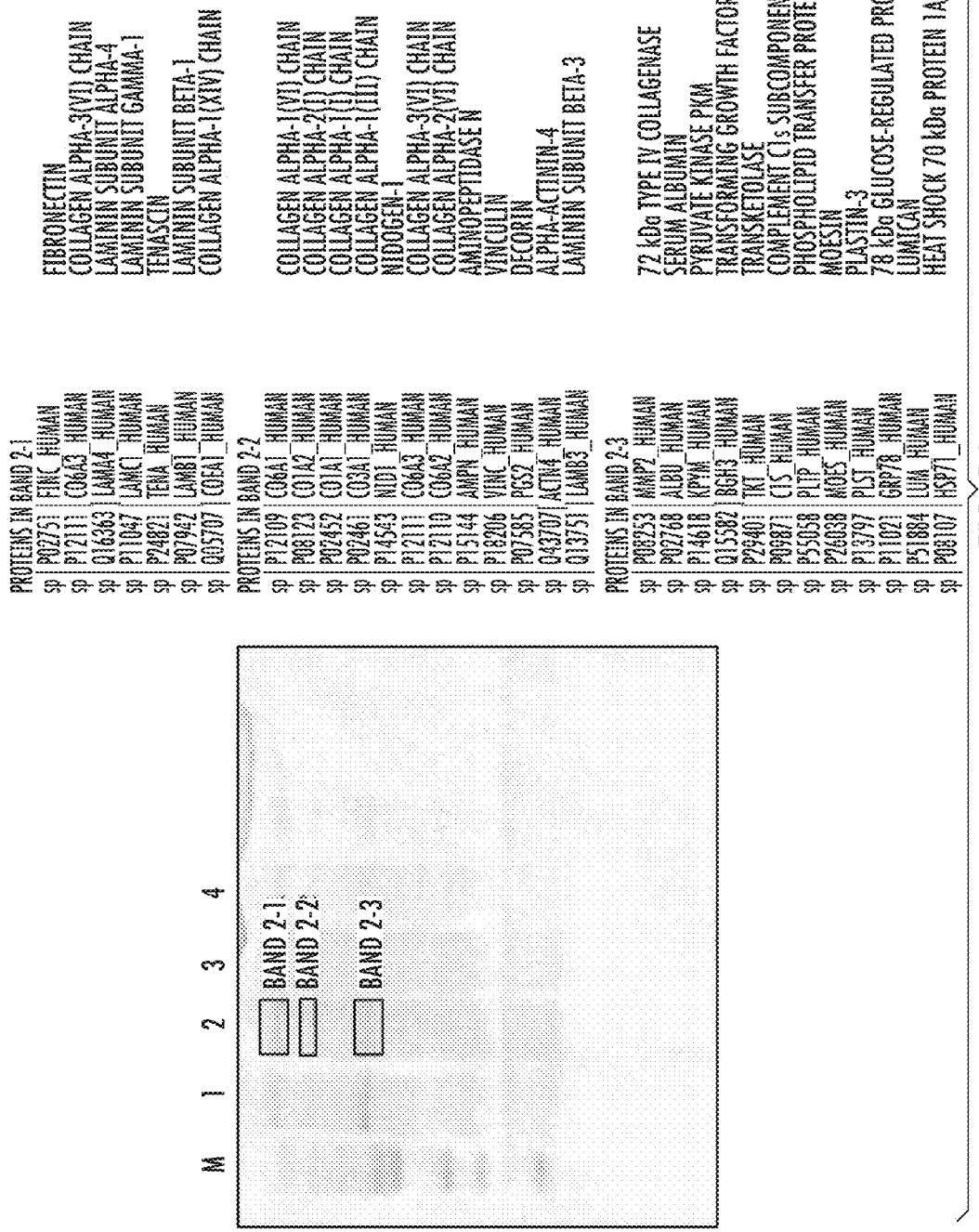
FIG. 14 shows the banding spectrum from an SDS-PAGE gel and the three bands that were excised for the Mass Spectrometry assay as well as the results from the Mass Spectrometry analysis.

As shown in FIG. 14 three samples (CM 1, CM 2, and CM 3) were subjected to SDS-PAGE protocol to isolate total protein. Three clear bands were detected prominently in the CM 2 sample (2-1, 2-2, and 2-3). The specific bands were excised and protein isolated from the gel which were then subjected to mass spectrometry to Mass Spectrometry to determine specific compounds in the serum.

As shown in FIG. 14, a number of beneficial compounds that are directly and/or associated with wound healing and skin rejuvenation were identified through the mass spectrometry assay in sample CM 2. The results of the mass spectrometry are attached as FIG. 14. For example, fibronectin, laminin, and collagen were detected in 2-1; collagen, nidogen, vinculin, and decorin were detected in 2-2, and moesin, plastin-3, and lumican were detected in 2-3.

Cosmetic Composition Embodiment

The following is an example formula for a cosmetic composition; in this case, a lotion.

Ingredients:
Water
Cetearyl Alcohol & Ceteareth-20
Glycerin
*Helianthus Annuus* (Sunflower) Seed Oil
Butyrospermum Parkii (Shea Butter)
Glyceryl Monostearate
Coconut (*Cocos Nucifera*) Oil
*Prunus Amygoalus Dulcis* (Sweet Almond) Oil.
Cetyl Alcohol
Phenoxetol
Vitamin E
Sodium Citrate
Carbomer
Plus
10% Vitamin C
Plus
10% KFS serum isolated using the procedures above
Plus
1,000,000 IU vit A per 40 g of lotion In addition to the above compounds, it is understood that a number of other compounds may be added to achieve various desirable qualities. For example, SPF may be added to the formulation for added UV protection. Additionally, sandalwood powder (e.g. 1 g of sandalwood per 6 g of lotion) may be added to generate more of an exfoliant quality.

In summation, KFS (Keratinocyte Fibroblast Serum) is a combination of compounds secreted by fibroblast and keratinocytes during culturing of these cells in sterile media without proteins or growth factor. Based on the compounds found using mass spectrometry and the other tests (including the MTT test), the serum is useful in several areas including, cosmetics, reduction and treatment of scars, wound healing, and burn therapy.

While the present invention has been described herein with respect to the exemplary embodiments, it will become apparent to one of ordinary skill in the art that many modifications, improvements and sub-combinations of the various embodiments, adaptations and variations can be made to the invention without departing from the spirit and scope thereof.

What is claimed is:

1. A method of making a cosmetic composition comprising combining water, vitamin C, vitamin A, and a human Keratinocyte Fibroblast Serum (KFS),
    wherein the human KFS is a compound mixture secreted by keratinocytes and fibroblasts in culture and substantially excludes other cell types, and wherein the human KFS is produced by the steps comprising:
    (1) obtaining a cell culture by culturing epithelial cells derived from human neonatal foreskin in a cell culture container, the cell culture container comprising a first media that contains nutrients and one or more exogenous growth factors selected from L-Glutamine, hydrocortisone hemisuccinate, linoleic acid, Lecithin, HSA, rh FGF β, rh EGF/TGF β-1, rh-insulin, and ascorbic acid, wherein the first media is free from porcine derived components,
    (2) culturing the cells in the first media until keratinocyte and fibroblast cells predominate a viable cell population in substantially equal proportions, and cells reach at least about 80 percent confluence,
    (3) removing the first media from the cell culture container and washing the cell culture cells with a buffer solution,
    (4) adding a volume of a sterile second media to the cell culture container, wherein the second media comprises nutrients of the first media but lacks exogenous growth factors of the first media, porcine-derived components, and bovine-derived components,
    (5) culturing the cells in the second media for a sufficient period of time to produce a conditioned media comprising at least one of fibronectin, laminin, collagen, nidogen, vinculin, decorin, moesin, plastin-3 and lumican,
    (6) removing and retaining a volume of the conditioned media from the cell culture container,
    (7) replacing the removed volume of conditioned media with an equal volume of the sterile second media,
    (8) repeating steps (6) and (7) at least once, and
    (9) combining the retained volumes of the conditioned media to produce the human KFS.

2. The method of claim 1, wherein steps (6) and (7) are repeated three times.

3. The method of claim 1, further comprising filtering the conditioned media and/or the human keratinocyte fibroblast serum with a micro filter.

4. The method of claim 1, wherein the first media is free from bovine derived components.

5. The method of claim 1, wherein the conditioned media substantially excludes components from cells other than human keratinocytes and human fibroblasts.

* * * * *